United States Patent
Armstrong et al.

(10) Patent No.: US 8,086,310 B2
(45) Date of Patent: Dec. 27, 2011

(54) POWER SUPPLY MONITORING FOR AN IMPLANTABLE DEVICE

(75) Inventors: Randolph K. Armstrong, Houston, TX (US); Albert W. Guzman, League City, TX (US); Huan D. Nguyen, Houston, TX (US)

(73) Assignee: Cyberonics, Inc., Houston, TX (US)

( * ) Notice: Subject to any disclaimer, the term of this patent is extended or adjusted under 35 U.S.C. 154(b) by 0 days.

(21) Appl. No.: 12/785,244

(22) Filed: May 21, 2010

(65) Prior Publication Data

US 2010/0274302 A1     Oct. 28, 2010

Related U.S. Application Data

(62) Division of application No. 10/902,221, filed on Jul. 28, 2004, now Pat. No. 7,751,891.

(51) Int. Cl.
*A61N 1/378* (2006.01)
(52) U.S. Cl. ............... 607/29; 607/4; 607/5; 607/27
(58) Field of Classification Search .......... 607/4–5, 607/27, 29
See application file for complete search history.

(56) References Cited

U.S. PATENT DOCUMENTS

| | | | | |
|---|---|---|---|---|
| 4,324,251 A | 4/1982 | Mann | | 128/419 |
| 5,352,968 A | 10/1994 | Reni et al. | | 320/35 |
| 5,713,931 A * | 2/1998 | Paul et al. | | 607/27 |
| 5,959,371 A * | 9/1999 | Dooley et al. | | 307/130 |
| 6,016,448 A | 1/2000 | Busacker et al. | | 607/29 |
| 6,453,198 B1 | 9/2002 | Torgerson et al. | | |
| 6,490,484 B2 | 12/2002 | Dooley et al. | | |
| 6,490,486 B1 | 12/2002 | Bradley | | |
| 6,553,263 B1 | 4/2003 | Meadows et al. | | |
| 6,620,186 B2 | 9/2003 | Saphon et al. | | |

(Continued)

FOREIGN PATENT DOCUMENTS

WO    WO 0108749    2/2001

OTHER PUBLICATIONS

PCT International Searching Authority; Search Report for International Application No. PCT/US2005/26514; Oct. 10, 2006; 4 pgs.

*Primary Examiner* — Niketa Patel
*Assistant Examiner* — Rex R Holmes
(74) *Attorney, Agent, or Firm* — Williams, Morgan & Amerson, P.C.; Jonathan D. Rowell; Darrell N. Fuller

(57) ABSTRACT

A method and an apparatus for projecting an end of service (EOS) and/or an elective replacement indication (ERI) of a component in an implantable device and for determining an impedance experienced by a lead associated with the implantable device. An active charge depletion of an implantable device is determined. An inactive charge depletion of the implantable device is determined. A time period until an end of service (EOS) and/or elective replacement indication (ERI) of a power supply associated with the IMD based upon the active charge depletion, the inactive charge depletion, and the initial and final (EOS) battery charges, is determined. Furthermore, to determine the impedance described above, a substantially constant current signal is provided through a first terminal and a second terminal of the lead. A voltage across the first and second terminals is measured. An impedance across the first and second terminals is determined based upon the constant current signal and the measured voltage.

23 Claims, 13 Drawing Sheets

U.S. PATENT DOCUMENTS

| | | |
|---|---|---|
| 6,648,823 B2 | 11/2003 | Thompson |
| 6,654,640 B2 | 11/2003 | Lyden |
| 6,658,294 B1 | 12/2003 | Zadeh et al. |
| 6,671,552 B2 | 12/2003 | Merritt et al. |
| 6,687,538 B1 | 2/2004 | Hrdlicka et al. |
| 6,721,600 B2 | 4/2004 | Jorgenson et al. |
| 6,745,077 B1 | 6/2004 | Griffith et al. |
| 6,748,273 B1 * | 6/2004 | Obel et al. .............. 607/29 |
| 6,760,624 B2 | 7/2004 | Anderson et al. |
| 6,760,625 B1 | 7/2004 | Kroll |
| 6,804,557 B1 | 10/2004 | Kroll |
| 6,820,019 B1 | 11/2004 | Kelly et al. |
| 2001/0034541 A1 | 10/2001 | Lyden .............. 607/29 |
| 2004/0039424 A1 | 2/2004 | Merritt et al. .............. 607/29 |
| 2004/0199146 A1 | 10/2004 | Rogers et al. .............. 604/891.1 |
| 2005/0088145 A1 | 4/2005 | Loch .............. 320/132 |

\* cited by examiner

POWER SUPPLY MONITORING FOR AN IMPLANTABLE DEVICE

CROSS-REFERENCE TO RELATED APPLICATIONS

This application is a divisional of patent application Ser. No. 10/902,221, filed Jul. 28, 2004 now U.S. Pat. No. 7,751,891.

BACKGROUND OF THE INVENTION

1. Field of the Invention

This invention relates generally to implantable medical devices, and more particularly to methods, apparatus, and systems for monitoring power consumption and impedance characteristics relating to implantable medical devices.

2. Description of the Related Art

There have been many improvements over the last several decades in medical treatments for disorders of the nervous system, such as epilepsy and other motor disorders, and abnormal neural discharge disorders. One of the more recently available treatments involves the application of an electrical signal to reduce various symptoms or effects caused by such neural disorders. For example, electrical signals have been successfully applied at strategic locations in the human body to provide various benefits, including reducing occurrences of seizures and/or improving or ameliorating other conditions. A particular example of such a treatment regimen involves applying an electrical signal to the vagus nerve of the human body to reduce or eliminate epileptic seizures, as described in U.S. Pat. No. 4,702,254 to Dr. Jacob Zabara, which is hereby incorporated by reference in its entirety in this specification. Electrical stimulation of the vagus nerve may be provided by implanting an electrical device underneath the skin of a patient and performing a detection and electrical stimulation process. Alternatively, the system may operate without a detection system if the patient has been diagnosed with epilepsy, and may periodically apply a series of electrical pulses to the vagus (or other cranial) nerve intermittently throughout the day, or over another predetermined time interval.

Many types of implantable medical devices, such as pacemakers and drug infusion pumps, typically include custom integrated circuits that are complex, expensive, and specific to the intended use. These systems also typically employ proprietary communications techniques to transfer information between the implant and an external programmer. The custom circuitry is developed because of the need to keep power consumption at a minimum, to conform to the allowable size for implantable devices, and to support the complexity of the detection and communication techniques, while still supplying the particular intended therapy.

Typically, implantable medical devices (IMDs) involving the delivery of electrical pulses to body tissues, such as pacemakers (heart tissue) and vagus nerve stimulators (nerve tissue), comprise a pulse generator for generating the electrical pulses and a lead assembly coupled at its proximal end to the pulse generator terminals and at its distal end to one or more electrodes in contact with the body tissue to be stimulated. One of the key components of such IMDs is the power supply, ordinarily a battery, which may or may not be rechargeable. In many cases surgery is required to replace an exhausted battery. To provide adequate warning of impending depletion of the battery and subsequent degradation of the operation of the IMD, various signals may be established and monitored. One such signal is an elective replacement indicator (ERI) that may indicate that an electrical device component, such as a battery, has reached a point where replacement or recharging is recommended. Another indicator may be an end of service (EOS) signal, which may provide an indication that the operation of the implanted device is at, or near, termination and delivery of the intended therapy can no longer be guaranteed. ERI and EOS are commonly used indicators of the present status of an IMD battery. ERI is intended to be a warning signal of an impending EOS indication, providing sufficient time (e.g., several weeks or months) in typical applications to schedule and perform the replacement or recharging.

Generally, battery-powered IMDs base the EOS and the ERI signals on battery voltage and/or battery impedance measurements. One problem associated with these methodologies is that, for many battery chemistries, these measured battery characteristics do not have monotonically-changing values with respect to remaining charge. For example, lithium/carbon monofluoride (Li/CFx) cells commonly used in neurostimulators and other IMDs have a relatively flat voltage discharge curve for the majority of their charge life, and present status of the battery cannot be accurately and unambiguously determined from a measured battery characteristic.

Another problem associated with this methodology is the variability of current consumption for a specific device's programmed therapy or circuitry. This variability, combined with the uncertainty of the battery's present status prior to ERI or EOS, hinders reliable estimation of the anticipated time until reaching ERI or EOS. For scheduling purposes, it is desirable to have a constantly available and reliable estimate over all therapeutic parameter ranges and operation settings of the time until the device will reach EOS, and provide an indication, similar in purpose to ERI, when that time reaches a specific value or range.

Impedance measurements are used to assess the integrity of the electrical leads that deliver the stimulation provided by a pulse generator. A change in the impedance across the leads that deliver the electrical pulses may be indicative either of changes in a patient's body or in the electrical leads themselves. For example, damage in the lead, which may be induced by a break in one or more filaments in a multifilament lead wire, or changes in the body tissue where stimulation is delivered, may affect the efficacy of the stimulation therapy. Therefore, it is desirable for changes in the lead impedance, which may be indicative of various changes or malfunctions, to be accurately detected.

For instance, the integrity of the leads that deliver stimulation is of interest to insure that the proper therapy dosage is delivered to the patient. Some IMDs, most notably pacemakers, provide a voltage-controlled output that is delivered to one or more body locations (such as the heart). Other IMDs, such as a vagus nerve stimulator device developed by Cyberonics, Inc., provide a current-controlled output. Generally, however, state-of-the-art measurements of lead impedance involve an analysis of the delivery of a voltage signal from a capacitive (C) energy storage component through the resistive (R) lead impedance and an examination of the decay of that signal based upon a time-constant proportional to the product of the resistance and capacitance (RC). The total equivalent impedance present at the leads and the known energy source total equivalent capacitance cause a time-constant discharge curve. As the voltage on the capacitance is discharged through the resistance, the exponential decay of this voltage may be monitored to determine the decay time constant RC. From that time constant and an estimate of the known equivalent capacitance C, the equivalent resistance R presented by the leads may be mathematically estimated.

However, this type of measurement may lead to inaccuracies for a number of reasons, including the fact that the discharging of the voltage signal may be affected by other resistances and capacitances in the system, the accuracy of the capacitor, the time, voltage, and algorithmic accuracies of the measurement system, and the like. It would be desirable to have a more efficient and accurate method, apparatus, and/or system to measure or assess the impedance present at the leads that deliver an electrical stimulation or therapy.

The present invention is directed to overcoming, or at least reducing, the effects of, one or more of the problems set forth above.

SUMMARY OF THE INVENTION

In one aspect of the present invention, a method is provided for projecting an end of service date and/or elective replacement indication of a power supply in an implantable medical device, the power supply having an initial electrical charge and a final electrical charge. According to a preferred embodiment, the method comprises determining an active charge depletion of an IMD, determining an inactive charge depletion of the implantable device, and determining a time period until an end of service (EOS) and/or elective replacement indication (ERI) of a power supply associated with the IMD based upon the active charge depletion, the inactive charge depletion, and the initial and final (EOS) battery charges.

In another embodiment, a method for projecting an end of service and/or an elective replacement indication of an IMD having a power supply with an initial electrical charge and a final electrical charge comprises determining a current usage rate for at least one future idle period, and determining charge depleted during at least one previous idle period. The method also comprises determining a current usage rate for at least one future stimulation period, and determining charge depleted during at least one previous stimulation period. A total charge depleted by the IMD is determined based upon the charges depleted during the at least one previous idle period and the at least one previous stimulation period, respectively. A total future charge depletion is determined based upon the current usage rate during the at least one future stimulation period and the current usage rate during the at least one future idle period. A time period until an end of service (EOS) and/or ERI of a power supply (e.g., a battery) of the IMD is determined based upon the total charge depleted and the total future charge depletion, as well as the initial and final (EOS) battery charges.

In a further embodiment of the present invention, a method is provided for projecting an end of service date and/or elective replacement indication of a power supply in an implantable medical device, the power supply having an initial electrical charge and a final electrical charge. According to a preferred embodiment, the method comprises determining a charge depletion of an IMD and determining a time period until an end of service (EOS) and/or elective replacement indication (ERI) of a power supply associated with the IMD based upon the charge depletion and the initial and final (EOS) battery charges.

In a further embodiment of the present invention, a method for projecting an end of service and/or elective replacement indication of an IMD having a power supply with an initial electrical charge and a final electrical charge comprises determining a previous active depleted charge of an IMD and determining a future or potential active current usage rate of the IMD. The method also comprises determining a previous inactive depleted charge of the IMD and determining a future or potential inactive current usage rate of the IMD. A time period until an EOS and/or ERI of a power supply associated with the implantable device is determined based upon the previous active depleted charge, the potential active current usage rate, the previous inactive depleted charge, the potential inactive current usage rate, and the initial and final (EOS) battery charges.

In another aspect of the present invention, an implantable medical device is provided for projecting an end of service and/or an elective replacement indication of a power supply in the IMD. The IMD comprises a battery with an initial electrical charge and a final electrical charge to provide power for at least one operation performed by the implantable device. The device further comprises a stimulation unit operatively coupled to the battery, the stimulation unit providing a stimulation signal to at least one body location. The stimulation unit preferably comprises an electrical pulse generator, but may alternatively comprise a drug pump, a magnetic field generator, a mechanical vibrator element, or other device for stimulating body tissue. The IMD also preferably comprises a controller operatively coupled to the stimulation unit and the battery. The controller is adapted to determine an active current usage rate and an inactive current usage rate of the IMD, as well as an active electrical charge depleted by the battery during stimulation and an inactive electrical charge depleted by the battery during inactive periods in which no electrical stimulation is provided to the patient. The controller is further adapted to determine a time period until an end of service of a power supply associated with the IMD based upon the active current usage rate and the inactive current usage rates, the active and inactive electrical charges depleted, and the initial and final electrical charges of the battery.

In still another aspect, the present invention comprises an IMD for projecting an EOS and/or an ERI of a battery. The IMD comprises a battery with an initial and a final (EOS) electrical charge, a stimulation unit providing an electrical stimulation signal, and a controller. The controller is adapted to determine first and second active current usage rates for current usage in a first stimulation therapy and a second stimulation therapy, respectively. The controller is also adapted to determine first and second inactive (i.e., non-stimulating) current usage rates in a first inactive mode and a second inactive mode, respectively. In addition, the controller is adapted to determine an active electrical charge depleted by the battery during stimulation and an inactive electrical charge depleted during inactive periods. The controller also determines a time period until an EOS and/or an ERI of the battery, based upon the first and second active current usage rates, the first and second inactive current usage rates, the active and inactive electrical charges depleted, and the initial and final electrical battery charges.

In another aspect of the present invention, a system is provided for projecting an EOS and/or an ERI of a power supply of an IMD. The system comprises an external device (i.e., a device outside the body of the patient) for performing remote communications with the IMD, and the IMD is also capable of communicating with the external device as well as delivering a stimulation signal to the patient. The IMD comprises a battery to provide power for delivering the stimulation signal, a communications unit to provide communications between the external device and the IMD, and a stimulation unit operatively coupled to the battery for providing a stimulation signal. The system also comprises a controller operatively coupled to the stimulation unit and to the battery. The controller comprises a charge depletion circuit for determining both an active charge depletion and an inactive charge depletion of the IMD. The controller further comprises an EOS/ERI circuit for determining a time period until an end of service and/or an elective replacement indication of a power supply associated with the implantable device, based upon the active charge depletion, the inactive charge depletion, and the original and EOS battery charges.

In yet another aspect of the present invention, a computer readable program storage device encoded with instructions is provided for projecting an end of service and/or an elective replacement indication of a power supply in an IMD. The computer readable program storage device is encoded with instructions that, when executed by a computer, determine an active charge depletion and an inactive charge depletion of the IMD, and also determines a time period until an end of service and/or an elective replacement indication of a power supply associated with the IMD based upon the determined active charge depletion, the determined inactive charge depletion, and the initial and final battery charges.

In another aspect of the present invention, a method is provided for determining an impedance presented by a lead associated with an IMD. In the method, a substantially constant current signal is provided through a first terminal and a second terminal of the lead. A voltage across the first and second terminals is measured, and an impedance across the first and second terminals is determined based upon the constant current signal provided and the measured voltage.

In another aspect of the present invention, an IMD is provided that comprises circuitry for determining an impedance presented by a lead associated with the IMD. The IMD comprises an amplifier circuit for providing a substantially constant current signal through a first terminal and a second terminal of a lead. The IMD further comprises a voltage measurement unit to measure a voltage across the first and second terminals. The implantable device additionally comprises an impedance determination unit to determine an impedance between the first and second terminals based upon the constant current signal and the voltage.

In another aspect of the present invention, a system is provided for determining an impedance experienced by a lead associated with an IMD. The system comprises an external device communicating with the IMD, and the IMD is in turn adapted to communicate with the external device and to deliver a stimulation signal to a lead coupled to the IMD. The IMD comprises an amplifier circuit for providing a substantially constant current signal through a first terminal and a second terminal of the lead. The IMD also includes a voltage measurement unit to measure a voltage across the first and second terminals, and an impedance determination unit to determine an impedance between the first and second terminals based upon the constant current signal and the measured voltage. The IMD may also include a communications unit for communicating data relating to the impedance determination to the external device.

In yet another aspect of the present invention, a computer readable program storage device encoded with instructions is provided for determining an impedance experienced by a lead coupled to an IMD. The computer readable program storage device is encoded with instructions that when executed by a computer, preferably within the IMD, provides a substantially constant current signal through a first terminal and a second terminal of the lead, measures a voltage across the first and second terminals, and determines an impedance across first and second terminals based upon the constant current signal and the voltage.

BRIEF DESCRIPTION OF THE DRAWINGS

The invention may be understood by reference to the following description taken in conjunction with the accompanying drawings, in which like reference numerals identify like elements, and in which.

Figure 1A:
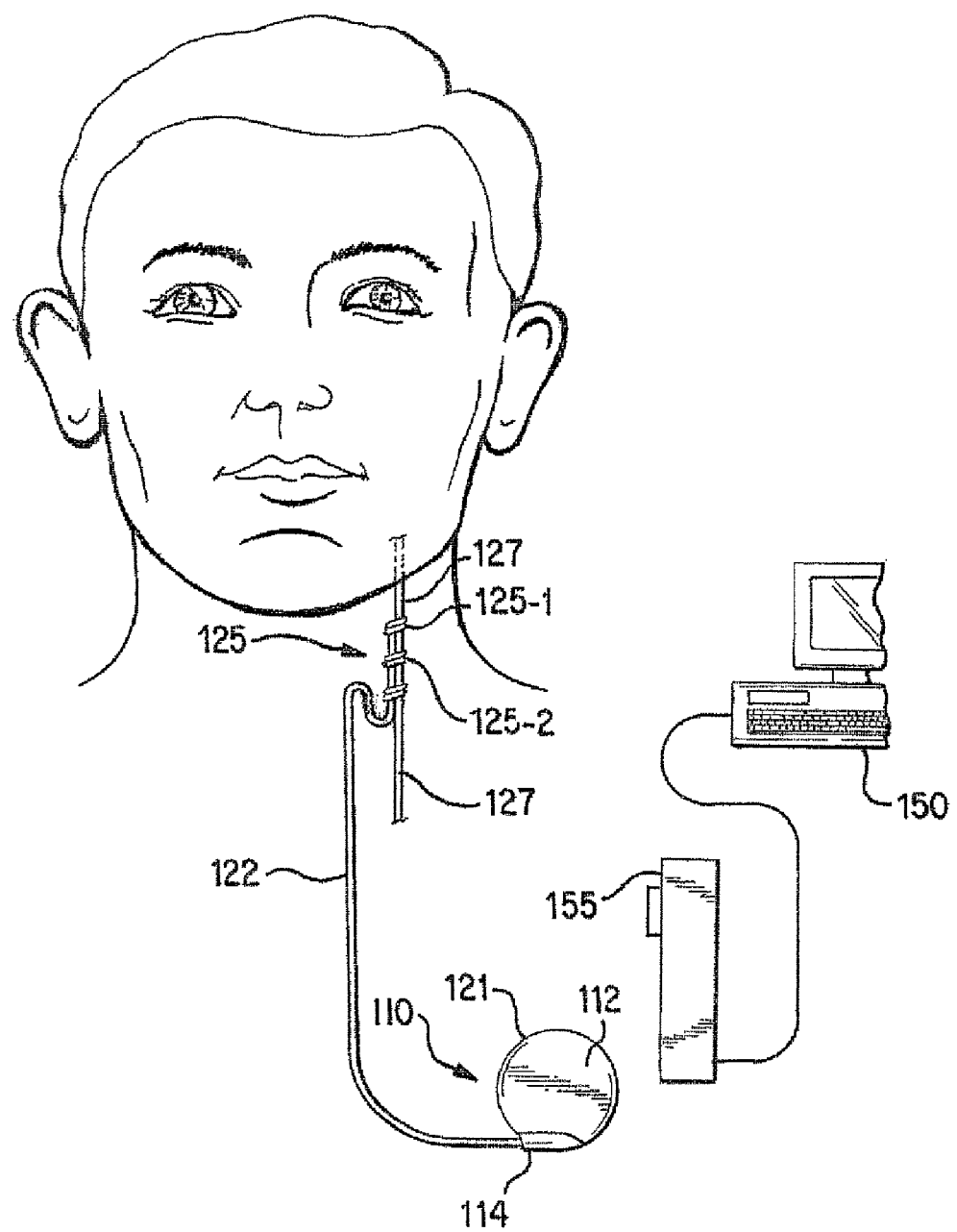
FIG. 1A is a stylized diagram of an implantable medical device suitable for use in the present invention implanted into a patient's body.
Figure 1B:
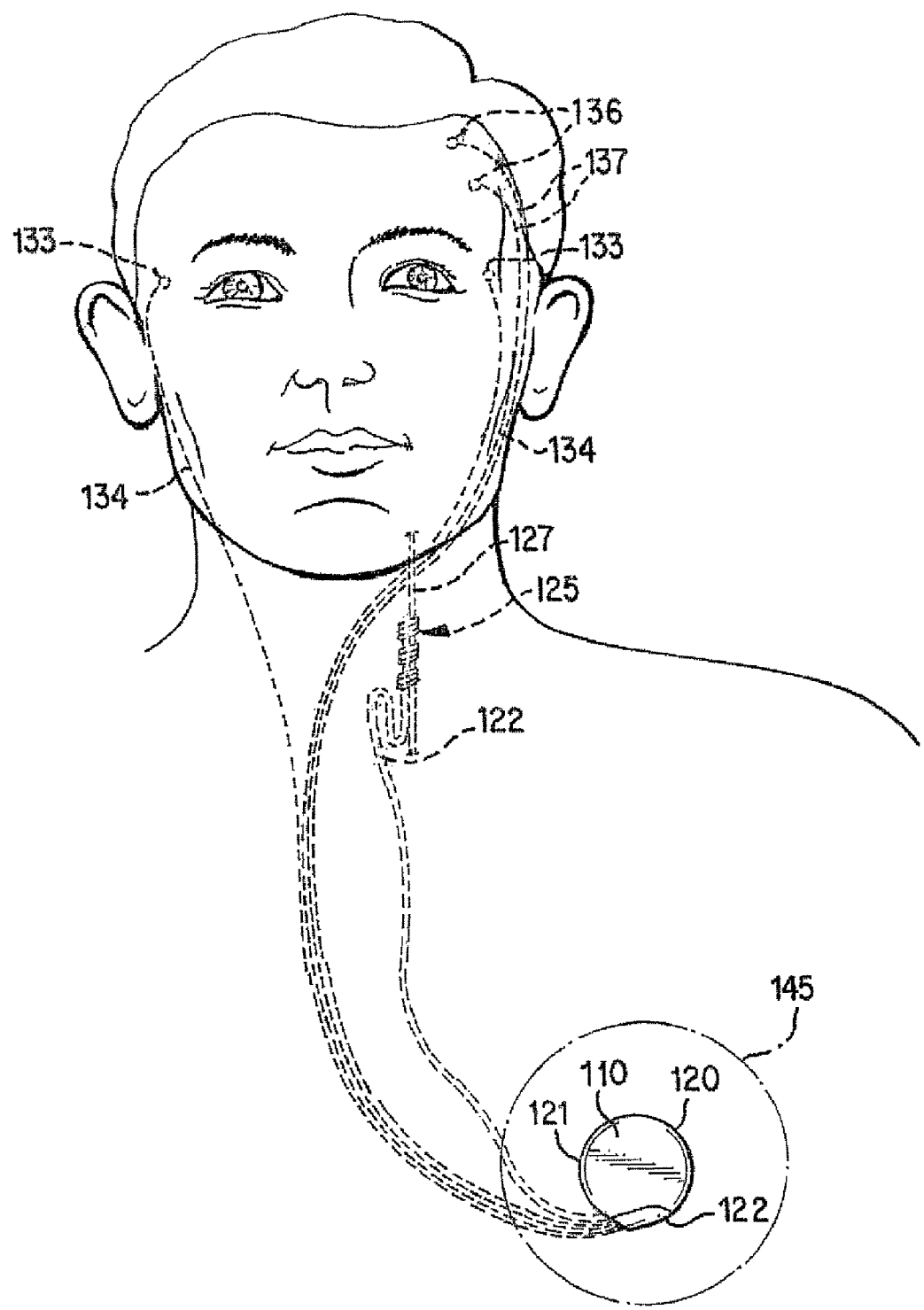
FIG. 1B is a stylized diagram of another embodiment of an implantable medical device suitable for use in the present invention implanted into a patient's body.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

DETAILED DESCRIPTION OF SPECIFIC EMBODIMENTS

Illustrative embodiments of the invention are described herein. In the interest of clarity, not all features of an actual implementation are described in this specification. In the development of any such actual embodiment, numerous implementation-specific decisions must be made to achieve the design-specific goals, which will vary from one implementation to another. It will be appreciated that such a development effort, while possibly complex and time-consuming, would nevertheless be a routine undertaking for persons of ordinary skill in the art having the benefit of this disclosure.

Embodiments of the present invention provide methods and apparatus for monitoring and/or estimating the electrical charge depletion of an implantable medical device (IMD). Estimating battery life may be based upon estimated future charge depletion and actual past charge depletion. Embodiments of the present invention provide for an elective replacement indicator (ERI) signal to provide a warning for performing an electrical diagnostic operation upon the IMD. This electrical diagnostic operation may include replacing an electrical component in the IMD, performing additional evaluation (s) of the operation of the IMD, replacing or recharging a power source of the IMD, and the like. A more detailed description of an IMD suitable for use in the present invention is provided in various figures and the accompanying description below.

Generally, IMDs contain power storage devices or battery units to provide power for the operations of the IMD. Embodiments of the present invention determine an estimated usable life remaining in the battery unit based upon determining initial and final battery charges, charge depleted by operations of the IMD, and a future depletion rate. Embodiments of the present invention may be performed in a standalone manner within the IMD itself, or in conjunction with an external device in communication with the IMD. Utilizing embodiments of the present invention, an end of service (EOS) signal or an ERI signal may be provided, indicating that the IMD is at or near termination of operations and/or the battery power has reached a level at which replacement should be considered to avoid interruption or loss of therapy to the patient.

Other embodiments of the present invention provide for determining the lead impedance. This process involves determining the voltage across a lead associated with the IMD, based upon the delivery of a constant current signal. The impedance may be measured on demand or at predetermined periodic intervals to detect significant changes in impedance across the leads of the IMD. Changes in the impedance may be logged and time-stamped, and saved in a memory in the IMD for diagnostic considerations. Voltage and current measurements associated with the IMD may be calibrated using various impedance measurements in order to enhance the accuracy of lead impedance measurements.

FIGS. 1A-1D illustrate a generator 110 having main body 112 comprising a case or shell 121 (FIG. 1A) with a connector 116 (FIG. 1C) for connecting to leads 122. The generator 110 is implanted in the patient's chest in a pocket or cavity formed by the implanting surgeon just below the skin (indicated by a dotted line 145), similar to the implantation procedure for a pacemaker pulse generator. A stimulating nerve electrode assembly 125, preferably comprising an electrode pair, is conductively connected to the distal end of an insulated electrically conductive lead assembly 122, which preferably comprises a pair of lead wires (one wire for each electrode of an electrode pair). Lead assembly 122 is attached at its proximal end to the connector 116 on case 121. The electrode assembly is surgically coupled to a vagus nerve 127 in the patient's neck. The electrode assembly 125 preferably comprises a bipolar stimulating electrode pair (FIG. 1D), such as the electrode pair described in U.S. Pat. No. 4,573,481 issued Mar. 4, 1986 to Bullara. Persons of skill in the art will appreciate that many electrode designs could be used in the present invention. The two electrodes are preferably wrapped about the vagus nerve, and the electrode assembly 125 is preferably secured to the nerve 127 by a spiral anchoring tether 128 (FIG. 1D) such as that disclosed in U.S. Pat. No. 4,979,511 issued Dec. 25, 1990 to Reese S. Terry, Jr. and assigned to the same assignee as the instant application. Lead assembly 122 is secured, while retaining the ability to flex with movement of the chest and neck, by a suture connection 130 to nearby tissue.

In one embodiment, the open helical design of the electrode assembly 125 (described in detail in the above-cited Bullara patent), which is self-sizing and flexible, minimizes mechanical trauma to the nerve and allows body fluid interchange with the nerve. The electrode assembly 125 preferably conforms to the shape of the nerve, providing a low stimulation threshold by allowing a large stimulation contact area with the nerve. Structurally, the electrode assembly 125 comprises two electrode ribbons (not shown), of a conductive material such as platinum, iridium, platinum-iridium alloys, and/or oxides of the foregoing. The electrode ribbons are individually bonded to an inside surface of an elastomeric body portion of the two spiral electrodes 125-1 and 125-2 (FIG. 1D), which may comprise two spiral loops of a three-loop helical assembly. The lead assembly 122 may comprise two distinct lead wires or a coaxial cable whose two conductive elements are respectively coupled to one of the conductive electrode ribbons 125-1 and 125-2. One suitable method of coupling the lead wires or cable to the electrodes comprises a spacer assembly such as that disclosed in U.S. Pat. No. 5,531,778, although other known coupling techniques may be used. The elastomeric body portion of each loop is preferably composed of silicone rubber, and the third loop 128 (which typically has no electrode) acts as the anchoring tether 128 for the electrode assembly 125.

In certain embodiments of the invention, eye movement sensing electrodes 133 (FIG. 1B) may be implanted at or near an outer periphery of each eye socket in a suitable location to sense muscle movement or actual eye movement. The electrodes 133 may be electrically connected to leads 134 implanted via a catheter or other suitable means (not shown) and extending along the jawline through the neck and chest tissue to the stimulus generator 110. When included in systems of the present invention, the sensing electrodes 133 may be utilized for detecting rapid eye movement (REM) in a pattern indicative of a disorder to be treated, as described in greater detail below.

Alternatively or additionally, EEG sensing electrodes 136 may optionally be implanted in spaced apart relation through the skull, and connected to leads 137 implanted and extending along the scalp and temple and then along the same path and in the same manner as described above for the eye movement electrode leads. Electrodes 133 and 137, or other types of sensors, may be used in some embodiments of the invention to trigger administration of the electrical stimulation therapy to the vagus nerve 127 via electrode assembly 125. Use of such sensed body signals to trigger or initiate stimulation therapy is hereinafter referred to as a feedback loop mode of administration. Other embodiments of the present invention utilize a continuous, periodic or intermittent stimulus signal applied to the vagus nerve (each of which constitutes a form of continual application of the signal) according to a programmed on/off duty cycle without the use of sensors to trigger therapy delivery. This type of delivery may be referred to as a prophylactic therapy mode. Both prophylactic and feedback loop administration may be combined or delivered by a single IMD according to the present invention. Either or both modes may be appropriate to treat the particular disorder diagnosed in the case of a specific patient under observation.

The pulse generator 110 may be programmed with an external computer 150 using programming software of the type copyrighted by the assignee of the instant application with the Register of Copyrights, Library of Congress, or other suitable software based on the description herein, and a programming wand 155 to facilitate radio frequency (RF) communication between the computer 150 (FIG. 1A) and the pulse generator 110. The wand 155 and software permit non-invasive communication with the generator 110 after the latter is implanted. The wand 155 is preferably powered by internal batteries, and provided with a "power on" light to indicate sufficient power for communication. Another indicator light may be provided to show that data transmission is occurring between the wand and the generator.

Figure 2:
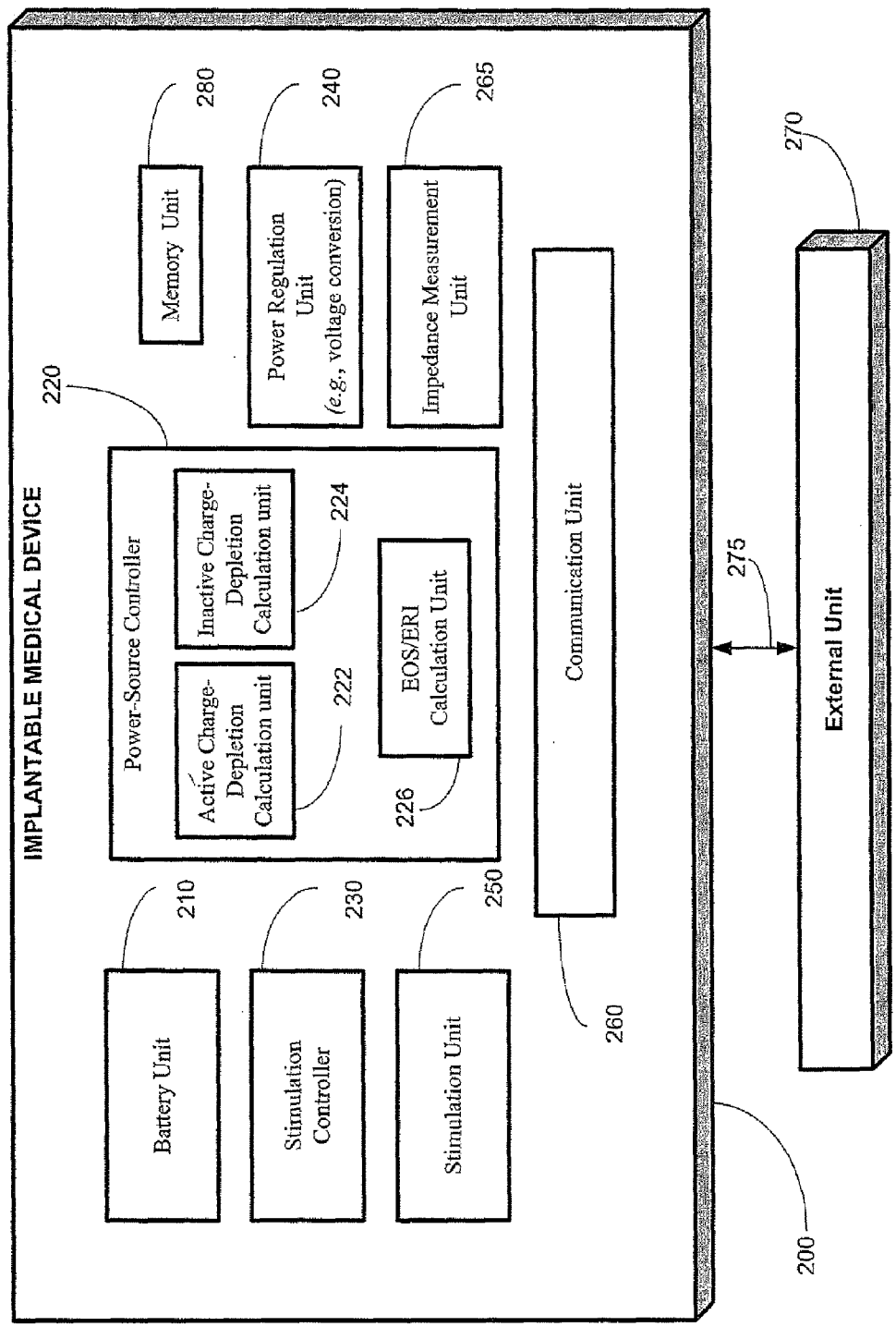
FIG. 2 is a block diagram of an implantable medical device and an external unit that communicates with the implantable medical device, in accordance with one illustrative embodiment of the present invention.

FIG. 2 illustrates one embodiment of an IMD 200 (which may comprise pulse generator 110) for performing neurostimulation in accordance with embodiments of the present invention. In one embodiment, the implantable medical device 200 comprises a battery unit 210, a power-source controller 220, a stimulation controller 230, a power regulation unit 240, a stimulation unit 250, an impedance measurement unit 265, a memory unit 280 and a communication unit 260. It will be recognized that one or more of the blocks 210-280 (which may also be referred to as modules) may comprise hardware, firmware, software, or any combination of the three. The memory unit 280 may be used for storing various program codes, starting data, and the like. The battery unit 210 comprises a power-source battery that may be rechargeable or non-rechargeable. The battery unit 210 provides power for the operation of the IMD 200, including electronic operations and the stimulation function. The battery unit 210, in one embodiment, may be a lithium/thionyl chloride cell or, more preferably, a lithium/carbon monofluoride (Li/CFx) cell. The terminals of the battery unit 210 are preferably electrically connected to an input side of the power-source controller 220 and the power regulation unit 240.

The power-source controller 220 preferably comprises circuitry for controlling and monitoring the flow of electrical power to various electronic and stimulation-delivery portions of the IMD 200 (such as the modules 230-265 and 280 illustrated in FIG. 2). More particularly, the power-source controller 220 is capable of monitoring the power consumption or charge depletion of the implantable medical device 200 and is capable of generating the ERI and the EOS signals. The power-source controller 220 comprises an active charge-depletion unit 222, an inactive charge-depletion unit 224, and an ERI/EOS calculation unit 226. The active charge-depletion unit 222 is capable of calculating the charge depletion rate of the implantable medical device 200 during active states, and may comprise sub-units to calculate the charge depletion rates of a plurality of active states comprising different charge depletion rates. The active state of the implantable medical device 200 may refer to a period of time during which a stimulation is delivered by the implantable medical device 200 to body tissue of the patient according to a first set of stimulation parameters. Other active states may include states in which other activities are occurring, such as status checks and/or updates, or stimulation periods according to a second set of stimulation parameters different from the first set of stimulation parameters. The inactive charge-depletion unit 224 is capable of calculating the charge depletion rate of the implantable medical device 200 during inactive states. Inactive states may also comprises various states of inactivity, such as sleep mode, wait modes, and the like. The ERI/EOS calculation unit 226 is capable of performing calculations to generate an ERI signal and/or an EOS signal. One or more of the active charge-depletion unit 222, the inactive charge-depletion unit 224, and/or the ERI/EOS calculation unit 226 may be hardware, software, firmware, and/or any combination thereof.

The power regulation unit 240 is capable of regulating the power delivered by the battery unit 210 to particular modules of the IMD 200 according to their needs and functions. The power regulation unit 240 may perform a voltage conversion to provide appropriate voltages and/or currents for the operation of the modules. The power regulation unit 240 may comprise hardware, software, firmware, and/or any combination thereof.

The communication unit 260 is capable of providing transmission and reception of electronic signals to and from an external unit 270. The external unit 270 may be a device that is capable of programming various modules and stimulation parameters of the IMD 200. In one embodiment, the external unit 270 is a computer system that is capable of executing a data-acquisition program. The external unit 270 is preferably controlled by a healthcare provider such as a physician, at a base station in, for example, a doctor's office. The external unit 270 may be a computer, preferably a handheld computer or PDA, but may alternatively comprise any other device that is capable of electronic communications and programming. The external unit 270 may be used to download various parameters and program software into the IMD 200 for programming the operation of the implantable device. The external unit 270 may also receive and upload various status conditions and other data from the IMD 200. The communication unit 260 may comprise hardware, software, firmware, and/or any combination thereof. Communications between the external unit 270 and the communication unit 260 may occur via a wireless or other type of communication, illustrated generally by line 275 in FIG. 2.

Stimulation controller 230 defines the stimulation pulses to be delivered to the nerve tissue according to parameters and waveforms that may be programmed into the IMD 200 using the external unit 270. The stimulation controller 230 controls the operation of the stimulation unit 250, which generates the stimulation pulses according to the parameters defined by the controller 230 and in one embodiment provides these pulses to the connector 116 for delivery to the patient via lead assembly 122 and electrode assembly 125 (see FIG. 1A). Various stimulation signals provided by the implantable medical device 200 may vary widely across a range of parameters. The Stimulation controller 230 may be hardware, software, firmware, and/or any combination thereof.

Figure 3:
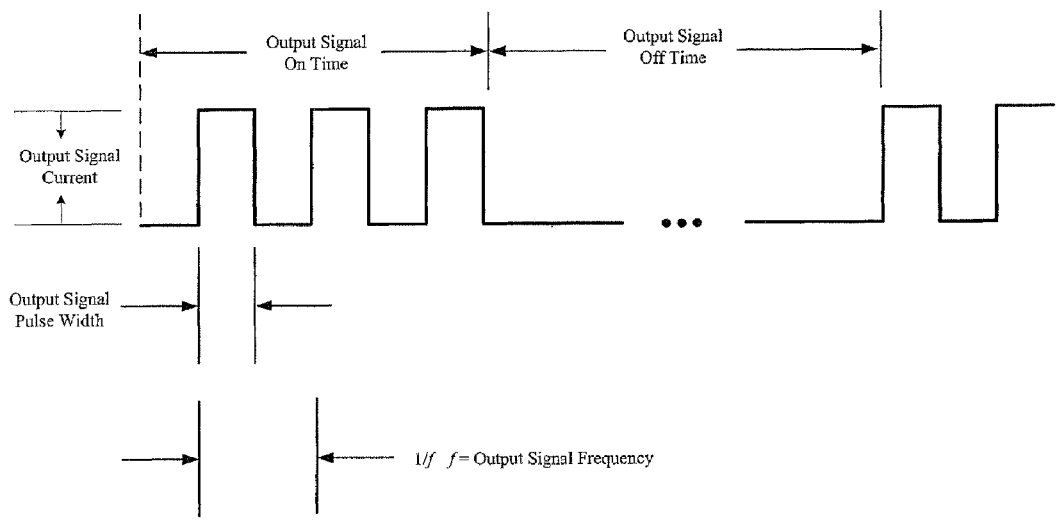
FIG. 3 is a stylized diagram of an output current signal provided by the implantable medical device of FIGS. 1 and 2, provided to illustrate certain stimulation parameters in accordance with one illustrative embodiment of the present invention.

FIG. 3 illustrates the general nature, in idealized representation, of an output signal waveform delivered by the output section of a pulse generator 110 (such as stimulation unit 250 shown in FIG. 2) to lead assembly 122 and electrode assembly 125 in an embodiment of the present invention. This illustration is presented principally for the sake of clarifying terminology, including the parameters of signal on-time, off-time, frequency, pulse width, and current. In the treatment of a neuropsychiatric disorder in an exemplary implementation, the stimulation unit 250 of the IMD 200 delivers pulses having a desired output signal current and frequency, with each pulse having a desired output signal pulse width. The pulses are delivered for the duration of the output signal on-time (stimulation period), and are followed by the output signal off-time during which no output signal is delivered (idle period). This periodic stimulation reduces the symptoms of the neuropsychiatric disorder. Stimulation parameters suitable for treatment of a variety of medical conditions can be found in the following patents: U.S. Pat. No. 4,702,254, U.S. Pat. No. 5,025,807, U.S. Pat. No. 4,867,164, and U.S. Pat. No. 6,622,088 (epilepsy); U.S. Pat. No. 5,188,104 and U.S. Pat. No. 5,263,480 (eating disorders); U.S. Pat. No. 5,215,086 (migraine headaches); U.S. Pat. No. 5,231,988 (endocrine disorders); U.S. Pat. No. 5,269,303 (dementia); U.S. Pat. No. 5,299,569 and U.S. Pat. No. 6,622,047 (neuropsychiatric disorders); U.S. Pat. No. 5,330,513 and U.S. Pat. No. 6,721,603 (pain); U.S. Pat. No. 5,335,657 (sleep disorders); U.S. Pat. No. 5,540,730 (motility disorders); U.S. Pat. No. 5,571,150 (coma); U.S. Pat. No. 5,707,400 (refractory hypertension); U.S. Pat. No. 6,587,719 and U.S. Pat. No. 6,609,025 (obesity); U.S. Pat. No. 6,622,041 (congestive heart failure). Each of the foregoing patents is hereby incorporated by reference herein in its entirety.

In one embodiment of the invention, the IMD 200 determines EOS and ERI values by using a known initial battery charge ($Q_0$) and a predetermined EOS battery charge ($Q_{EOS}$) indicative of the end of useful battery service, together with the charge actually depleted ($Q_d$) by the IMD (calculated from the current usage rates for idle and stimulation periods ($r_i$ and $r_s$), and the length of the respective idle and stimulation periods), to calculate for a desired time point how much useful charge remains on the battery ($Q_r$) until the EOS charge is reached, and how long at projected current usage rates the device can operate until EOS or ERI. Once the charge actually depleted by operation of the device ($Q_d$) is known, the current usage rates are then applied to the remaining useful charge $Q_r$ to determine the time remaining until EOS and/or ERI.

The present invention allows EOS and ERI determinations to be made without measurements or calculations of internal battery impedance or other battery parameters. Instead, the device maintains a precise record of the current used during idle and stimulation periods, and subtracts the charge represented by the current used from the total available battery charge to determine the charge remaining on the battery. Because the relative duration of stimulation and idle periods are determined by the stimulation programming parameters of the IMD, a determination of EOS and ERI can be calculated in a straightforward manner based upon the current usage rates associated with the programming parameters.

Figure 4:
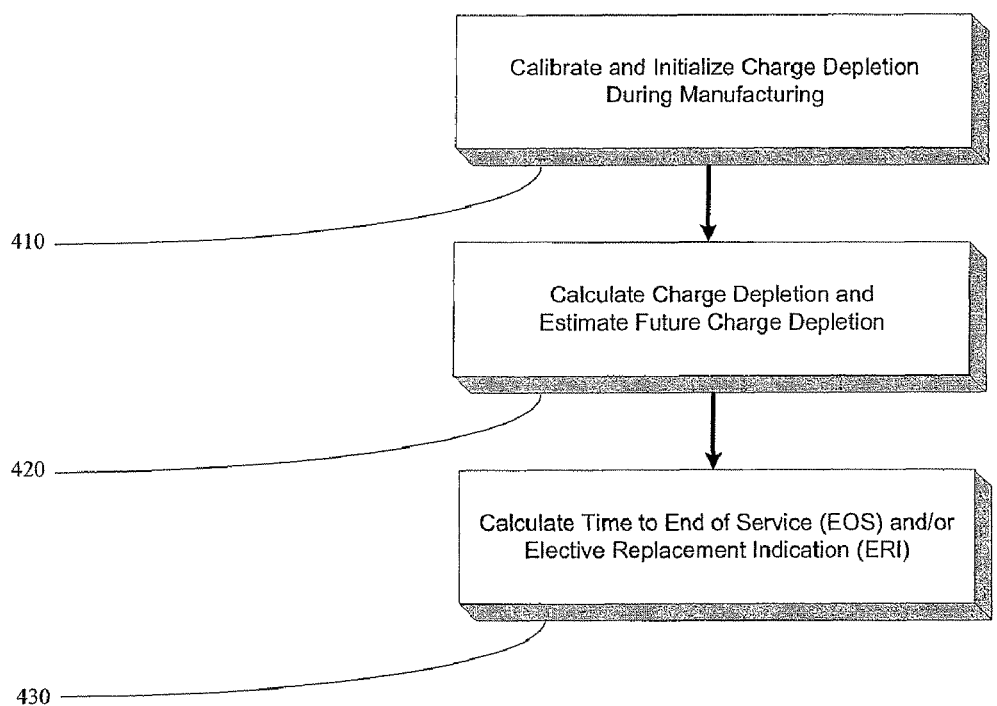
FIG. 4 is a flowchart representation of a method of providing a warning signal relating to a power supply of the implantable medical device, in accordance with one illustrative embodiment of the present invention.

Consistent with the foregoing, FIG. 4 provides a flowchart depiction of a method for determining the remaining time to EOS and/or ERI based on known or determined IMD characteristics such as battery charge and current usage rates. In one embodiment, the current usage of the IMD 200 is calibrated during manufacture (step 410). Current drawn by the IMD from the battery is defined as electrical charge per unit time. The total charge depleted from the battery as a result of the operations of the IMD may be determined by multiplying each distinct current rate used by the IMD by its respective time used. In one embodiment, as part of the calibration, during manufacturing, a power supply capable of generating known currents and voltages may be used to characterize the power consumption or current depletion of the implantable medical device 200 during its stimulation and idle modes The power consumption data thus obtained is preferably stored in a memory of the IMD.

Once the charge usage characteristics of the IMD are known, the battery may be subsequently installed into the implantable medical device 200 for operation and thereafter a record of power consumed by the implantable medical device 200 is maintained. In a particular embodiment, the calibration step 410 involves calibration of current usage for idle periods ($r_i$) and stimulation periods ($r_s$) of the device. Current may thus be used as a proxy value for electrical charge depletion, and the calibration step allows a precise determination of the amount of electrical charge used by the device after implantation. As used herein, the terms "depletion rate," "consumption rate," and "usage rate" may be used interchangeably and refer to the rate at which electrical charge is depleted from the battery. However, as noted above, current may be used as a proxy for electrical charge, and where this is the case, current rates $r_i$ and $r_s$ may also be referred to as "current usage," "current rate," "current consumption," "charge depletion," "depletion rate" or similar terms.

As previously noted, the IMD 200 has a number of settings and parameters (e.g., current, pulse width, frequency, and on-time/off-time) that can be changed to alter the stimulation delivered to the patient. These changes result in different current usage rates by the IMD 200. In addition, circuit variations from device to device may also result in different current usage rates for the same operation. Calculations and estimations are preferably performed during the manufacturing process in order to calibrate accurately and precisely the current usage rates of the IMD 200 under a variety of stimulation parameters and operating conditions. A calibration of the current usage rates and a determination of the charge present on the battery at the time of implant allow a more accurate assessment of actual and predicted charge depletion after the IMD 200 is implanted. The initial charge on the battery may include a safety factor, i.e., the charge may be a "minimum charge" that all batteries are certain to possess, even though many individual batteries may have a significantly greater charge. Nothing herein precludes a determination of a unique initial charge for each individual battery. However, it will be recognized that such individual determinations may not be economically feasible. A more detailed illustration and description of the step (410) of calibrating current usage and initializing the battery charge for the implantable medical device 200 is provided in FIG. 5 and the accompanying description below.

After calibrating the current usage characteristics of the IMD 200, the IMD may be implanted and subsequently a charge depletion calculation is performed (step 420). This calculation may be performed by the IMD itself, the external unit 270, or by both, and includes determining the actual electrical charge depleted from the battery 210 and estimating future current usage (i.e., depletion rates), which are then used to calculate an elective replacement indication (ERI) and/or an end of service (EOS) signal (step 430). A more detailed illustration and description of the step 420 of calculating the electrical charge depleted is provided in FIG. 6 and the accompanying description below. In step 430 an estimated time until an elective replacement indication will be generated and/or the estimated time until the end of service are calculated utilizing the initial battery charge, the actual charge consumed and the estimated future charge depletion calculated in light of the calibration performed during manufacture. A more detailed description and illustration of the step 430 of calculating the time to ERI and/or EOS is provided in FIG. 7 and the accompanying description below.

Figure 5:
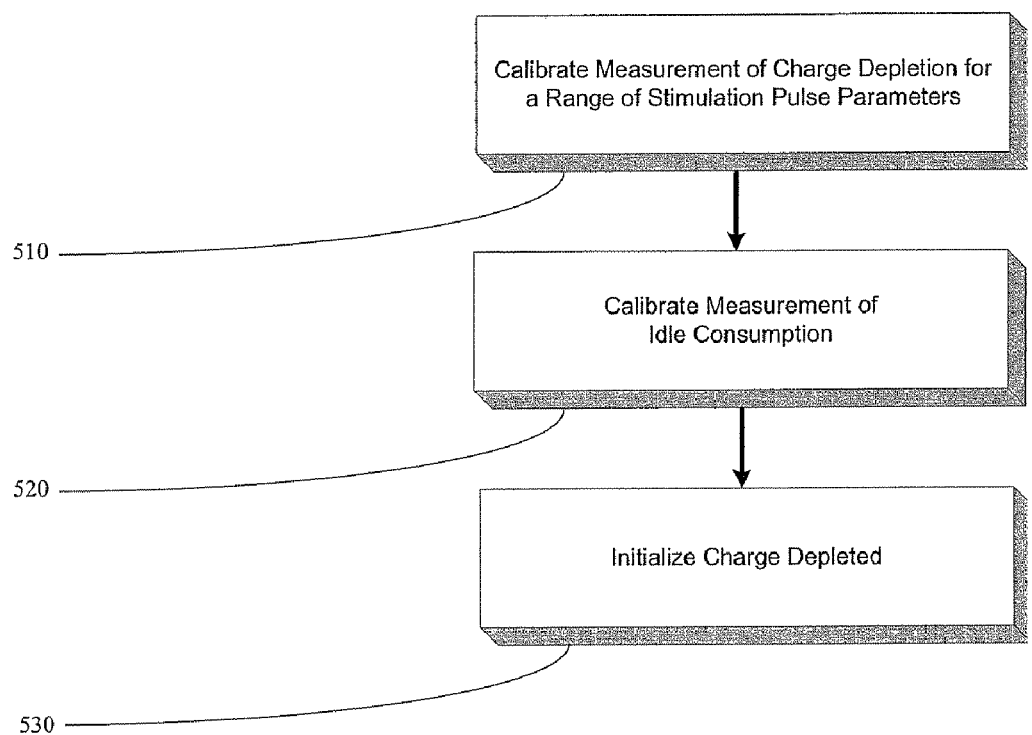
FIG. 5 is a flowchart representation of a method of performing a calibration of a charge depletion tabulation, in accordance with one illustrative embodiment of the present invention.

Referring now to FIG. 5, a flowchart diagram is provided depicting in greater detail the step 410 (FIG. 4) of calibrating and initializing the IMD 200 during manufacturing. In one embodiment, the current rates for the IMD 200 during stimulation are calibrated (block 510). During manufacturing, several different combinations of measurements may be calibrated. More specifically, measurements of charge depletion relating to different types of pulses (i.e., pulses having different stimulation parameters) are calibrated to ensure that current usage measurements for the IMD are accurate over a wide range of stimulation parameters. In other words, various pulses having a range of current amplitudes, pulse widths, frequencies, duty cycles and/or lead impedances into which the pulses are delivered are used to calibrate the measurement of current usage during stimulation to establish a baseline of the measurement of charge depletion for various types of pulses. All operational variables relating to or affecting the current usage rates of the IMD may be considered.

More particularly, during manufacture of the IMD 200, several combinations of data points relating to various current rates resulting from various combinations of pulse parameters are used in one embodiment to generate a linear equation that relates various pulse parameters to current rate, which may then be used to determine charge depletion. For example, for a first stimulation, pulses of a certain frequency are provided and for a second stimulation, the frequency of the pulses used may be doubled. Therefore, the estimated current usage rate for the second stimulation may be estimated to be approximately double that of the power consumption or charge depleted due to the first stimulation. As another example, a first stimulation may be of a first pulse width and a second stimulation may be of a pulse width that is double that of the width of the first pulse. Therefore, a relationship between the pulse width to the current consumption of the second pulse may be estimated to be approximately double that of the current usage rate of the first pulse. In one embodiment, a graph may be generated using the various types of stimulation versus the current consumption associated with that stimulation.

As yet another example, a first stimulation pulse may have a first current amplitude and a second stimulation may have a current amplitude that is double that of the first stimulation pulse. Therefore, the current consumption of the second stimulation pulse may be estimated to be approximately double that of the current consumption of the first stimulation pulse. The power consumption is directly proportional to the current consumption. Therefore, a relationship of a pulse parameter to current usage rate may be estimated or measured such that an interpolation may be performed at a later time based upon the linear relationship developed during the calibration of the power consumption during stimulation. It may be appreciated that the relationships of some pulse parameters to current usage rate may not be a simple linear relationship, depending upon such pulse characteristics as the type of pulse decay (i.e., square wave, exponential decay), for example. Nevertheless, calibration of current usage rate for various pulse parameters may be performed by routine calculation or experiment for persons of skill in the art having the benefit of the present disclosure.

Referring again to FIG. 5, current usage during an idle (i.e., non-stimulating) period is calibrated in step 520. From the idle current consumption and the stimulation current consumption calibration, the overall current consumption may be modeled based upon programmed settings. It should be noted that while the invention as shown in the drawings describes a device having two current usage patterns associated with an idle period and a stimulation period, such a two-state embodiment is described solely for clarity, and more complex embodiments are possible involving a third state such as, by way of nonlimiting example, a current usage rate associated with electrical sensing of the lead electrodes, which may be defined by a third current rate $r_3$. Four-state or even higher state embodiments are possible, although where the differences in current usage rates are small, or where a particular current usage rate comprises only a tiny fraction of the overall time of the device, the complexity required to implement and monitor the time such current rates are actually used by the device may render the device impractical. These multi-state embodiments may be implemented if desired, however, and remain within the scope and spirit of the present invention.

Using the calibration of current usage during stimulation periods (step 510) and idle periods (step 520), a calculation may optionally be made to initialize the charge depleted, if any, during manufacturing operations, such as the charge depleted during testing of the device after assembly (block 530). In a preferred embodiment, all of the calibrations are performed with a calibrated current source device, and not a battery, and in this case there is no charge depletion during manufacturing operations. In another embodiment, the amount of charge depleted during manufacturing may small, in which case the initialization procedure may also be omitted. The calibration and/or initialization steps of FIG. 5 allow the IMD 200, via power-source controller 220, to maintain a running tally of how much charge has been depleted from the device. When the battery unit 210 is first inserted into the implantable medical device 200, the charge depleted is generally initialized to zero so that a running tabulation may begin from zero for maintaining a running tally of the charge depleted from the battery over the life of the implantable medical device 200. In one embodiment, the charge depleted tally is incremented throughout the operating life of the device and at any point the running tally may be subtracted from the known initial charge of the battery to determine the remaining charge. In an alternative embodiment, the charge depleted tally could be initialized to the value of the battery initial charge and the tally decremented throughout the device operation and directly used as the remaining charge. In either implementation, information relating to the baseline charge remaining on the battery at the end of manufacturing may be retained to calculate the estimated time to EOS or ERI.

Figure 6:
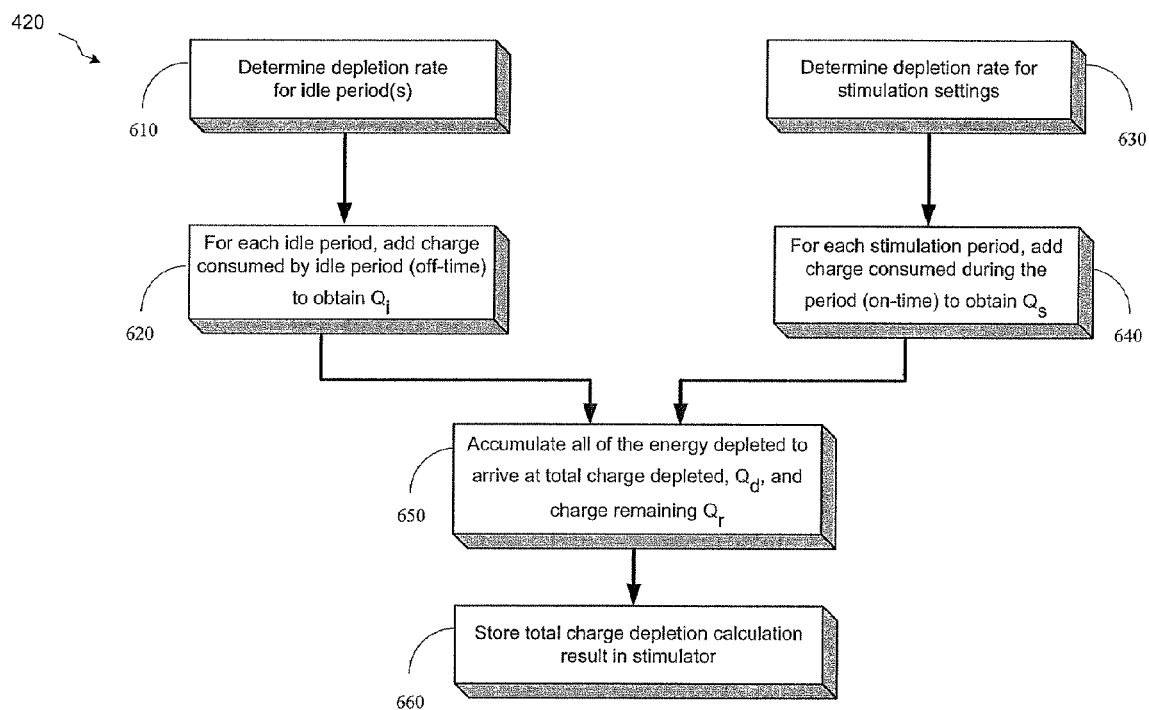
FIG. 6 is a more detailed flowchart illustrating a method of performing the charge depletion calculation indicated in FIG. 4, in accordance with one illustrative embodiment of the present invention.

Turning now to FIG. 6, a flowchart depiction of the step 420 of calculating charge depleted by the device is provided in greater detail. For simplicity, only the two-current state of a single idle period and a single stimulation period is shown. Embodiments having additional current usage rates are included in the present invention. The IMD 200 may determine a current depletion rate $r_i$ for idle periods (block 610). The rate is preferably stored in memory. In one embodiment, the determination is made by the IMD 200 after implantation. In a preferred embodiment, the idle current depletion rate may be a rate determined during manufacturing (i.e., a rate calibrated in step 520) and stored in the memory 280. An idle period is defined as a time period when the implantable medical device 200 is not performing active stimulation, i.e., is not delivering a stimulation pulse to the electrodes. Various electronic functions, such as tabulation and calculation of numbers or execution of various software algorithms within the IMD 200 may take place during the idle period.

As noted, the current rate $r_i$ during idle periods 610 may be predetermined during the manufacturing process (step 520) and may include various considerations, such as the power consumption of the operation of various electronics in the implantable medical device 200, even though no active stimulation may be taking place during that time period. However, since the implantable medical device 200 may be occasionally reprogrammed while still implanted inside a patient's body, the number and duration of idle periods may vary according to the duty cycle and frequency of the stimulation pulses. Therefore, the IMD 200 (e.g., via the power source controller 220 in the device) may maintain a running tabulation of the idle periods, and for each idle period a certain amount of charge depleted during the idle period (i.e., off time) is tabulated and stored in memory 280 (step 620).

It will be appreciated that the depleted charge may be obtained in a number of different ways, each within the scope of the present invention. Specifically, the total time of all idle periods since implantation, initialization, or since a previous idle power depletion calculation, may be maintained as a running total idle time in memory, or alternatively a running tally of charge depleted during idle periods may be maintained. While these values are different numerically, they are directly related by simple equations as discussed more fully hereinafter. At an update time, the total idle time may be periodically accessed and multiplied by the idle period current usage rate to determine the total power depleted during idle periods since implantation, initialization, or the previous calculation.

The IMD 200 may also maintain in memory 280 a tabulation of current usage rates (i.e., charge depletion) for a wide range of stimulation settings (step 630). In another embodiment, theoretical charge depletion calculations relating to particular types of stimulation may be provided to the IMD 200. The stimulation parameter settings may then be used by the device to maintain a running tabulation of the charge depleted during stimulation periods using a current usage rate $r_s$ calculated from the pulse width, pulse amplitude, pulse frequency, and other parameters which may impact the current usage rate. This method provides specific current usage rates for a variety of stimulation parameter settings and lead impedances without requiring the storage of current usage rates for all possible stimulation parameter settings and lead impedances.

In one embodiment, the charge depleted may be stored in micro-amp seconds; however, various other measurement units may be utilized. In one embodiment, the IMD 200 itself may be capable of calculating the current usage rate for a particular combination of programmed output settings based upon a known relationship between current usage rates and different combinations of programmed settings. The relationship may then be used to interpolate a particular current usage rate for a particular combination of programmed output settings. However, in order to reduce the computation load on the device, some or all of these calculations, including the interpolation, are preferably performed by an external programmer 270. Therefore, upon programming or performing routine maintenance of the implantable medical device 200, the external unit 270 may perform the calculations to determine the current usage rate during future stimulation cycles based upon the settings implemented during the programming or maintenance operation.

For example, if the stimulation for a particular patient is set to a particular pulse width, the external device 270 may factor in the calibration data and determine a current usage rate for a particular set of stimulation settings. Therefore, for each stimulation period, the charge that is depleted is tabulated for the stimulation period ("on-time") by multiplying the stimulation time by the current usage rate and a running tabulation is maintained (block 640). For example, if the predetermined current usage rate for each second of stimulation at a particular combination of parameter settings is 100 microamps, and the stimulation is 30 seconds long, a calculation is made by multiplying the 30 second time period for the stimulation, by the 100 microamps to arrive at 3000 micro amp seconds of charge consumed, which is then added to a running charge consumption tally.

As illustrated in FIG. 6, the sum of the tabulations of the charge depleted for the idle period (off-time or inactive period; step 620) and the charge depleted for the stimulation period (on-time or active period; step 640) are added to arrive at a total charge depleted by the IMD 200 (block 650). It will be appreciated that the sum of idle period and stimulation charge depletion may occur at the conclusion of one or more cycles of idle period and stimulation period, or continuously throughout idle periods and stimulation periods. Occasionally during the operational life of the IMD 200, various stimulation parameters may be changed to provide different types of stimulation. However, utilizing the steps described herein, a running tally (or a periodically updated tally) of the charge depletion is maintained, such that even when the stimulation settings change, the device maintains a substantially accurate reflection of the actual charge that has been depleted by the IMD 200, and future depletion calculations are based on the depletion rate for the newly programmed settings.

The memory 280 may store the results of the charge calculations (step 660). The data stored may include both the current usage rates for idle and stimulation periods of the IMD 200, as well as the total charge depleted. This data may be utilized by the IMD 200 and/or external unit 270 to determine various aspects of the device, including the amount of remaining battery life.

The calculations associated with steps 620, 640 and 650 may be expressed mathematically. In particular, the total charge available from the battery $Q_{tot}$ after it is placed in the IMD 200 may be represented as the difference between an initial battery charge $Q_0$ and the EOS battery charge $Q_{EOS}$, as expressed in Equation 1.

$$Q_{tot} = Q_0 - Q_{EOS} \qquad \text{Equation 1}$$

The charge depleted by the IMD 200 during idle periods $Q_i$ (step 620) may be expressed as the idle period current usage rate $r_i$ multiplied by the total duration of all idle periods $\Delta t_i$ according to equation 2.

$$Q_i = r_i \times \Sigma \Delta t_i \qquad \text{Equation 2}$$

Where multiple idle rates are present, the above equation will be solved for each idle current usage rate and the results summed to obtain $Q_i$. Similarly, the charge depleted during stimulation periods $Q_s$ (step 640) may be expressed as the stimulation period current usage rate $r_s$ multiplied by the total duration of all stimulation periods $\Delta t_s$ according to equation 3.

$$Q_s = r_s \times \Sigma \Delta t_s \qquad \text{Equation 3}$$

Again, where multiple stimulation rates are used the equation will be solved for each stimulation rate and the results summed. The total charge depleted $Q_d$ is the sum of $Q_i$ and $Q_s$, as shown in equation 4.

$$Q_d = Q_i + Q_s \qquad \text{Equation 4.}$$

Finally, the charge remaining until EOS ($Q_r$) at any arbitrary point in time is the difference between the total energy or charge available $Q_{tot}$ and the charge actually depleted from the battery $Q_d$ at that same timepoint, as expressed in equation 5 (step 650).

$$Q_r = Q_{tot} - Q_d \qquad \text{Equation 5}$$

This may be accomplished by counters that record the amount of time the device uses the idle current usage rate(s) and the stimulation current usage rate(s), respectively, which are then multiplied by the applicable current usage rate to obtain the total consumed charge during the idle and stimulation periods. Alternatively, separate registers may directly maintain a running tally of the charge depleted during stimulation periods and idle periods, respectively.

Figure 7:
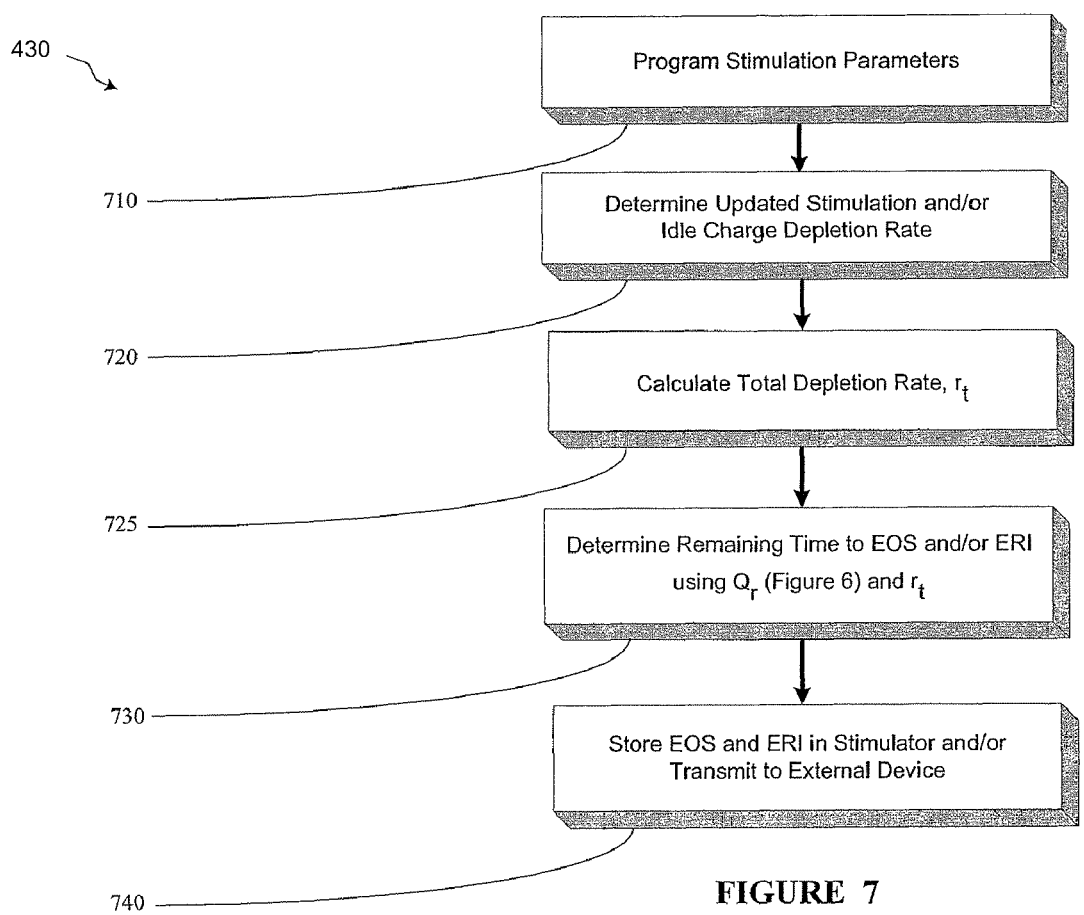
FIG. 7 is a more detailed flowchart illustrating a method of performing an end-of-service (EOS) and/or an elective replacement indication (ERI) determination, as indicated in FIG. 4, in accordance with one illustrative embodiment of the present invention.

Turning now to FIG. 7, a more detailed flow chart depicting the calculation of the time to the end of service (EOS) and/or elective replacement indicator (ERI) signals, as indicated in step 430 of FIG. 4, is illustrated. The IMD 200 is programmed for delivering to the patient electrical pulses having predetermined parameters (step 710). Programming the stimulation settings may be performed during manufacturing and/or by a healthcare provider when the external unit 270 gains communication access to the IMD 200. Occasionally, medical personnel may determine that an alteration of one or more of the stimulation parameters is desirable. Implementation of such changes may easily be accomplished to optimize the therapy delivered by the IMD. Alternatively, as part of a routine diagnostic process, a predetermined change to the stimulation settings may be performed. Additionally, the IMD 200 may have multiple sets of stimulation parameters stored in memory and may switch between the different stimulation modes represented by those parameters at preset times or at the occurrence of certain physiological events. When a change in one or more stimulation parameter settings is implemented (whether by programming or accessing data from memory), the IMD 200 and/or the external unit 270 may determine an updated stimulation period current usage rate $r_s$ associated with the new parameter settings, and subsequent updates to the total charge consumed will be based upon the new stimulation period current usage rate (step 720). The rates may either be stored in memory or calculated from an equation by interpolation among known current rates for known parameter settings, as previously described. It is also possible that changes to the software or firmware of the device could change the idle period depletion rate, in which event a new idle period current usage rate $r_i$ may also be calculated and reflected in subsequent calculations of total charge depleted (step 720).

Because the duty cycle (on-time to off-time ratio) is also a programmed parameter, the present invention allows both the idle period current usage rate ($r_i$) and the stimulation period current usage rate ($r_s$) to be combined into a single rate for purposes of projecting future energy or charge depletion and calculating a time to EOS and/or ERI. This rate represents the total current usage rate ($r_t$) of the device (step 725). Following updates to the stimulation and/or idle period current usage rates $r_s$ and $r_i$, the updated rates are then used to calculate a new total charge remaining $Q_r$, by a method substantially as shown in FIG. 6 and previously described. Once the total charge remaining is retrieved from memory, the remaining time to an activation of an EOS is calculated (step 730) by using the total depletion rate $r_t$ and the total charge remaining $Q_r$ on the battery until EOS. More particularly, the time remaining is calculated by dividing the remaining charge by the total depletion rate as shown in Equation 6.

$$t = Q_r / r_t \qquad \text{Equation 6}$$

At a predetermined time period before the end of service of the battery unit 210 is reached, an ERI signal, which may prompt the healthcare provider and/or the patient to schedule elective replacement of an electronic device, may be asserted to provide a warning. ERI is typically determined as simply a predetermined time, for example from 1 week to 1 year, more typically 6 months, earlier than EOS. In an alternative embodiment, the ERI signal may be defined as a particular charge level remaining ($Q_{ERI}$) above the EOS charge, $Q_{EOS}$. In this embodiment, the time period remaining until the ERI signal could be calculated by dividing $Q_{EOS}$ by the total depletion rate $r_t$ and subtracting the resulting time period from the time to EOS as calculated in equation 6.

The time to EOS provides a warning to the healthcare provider and/or patient that the energy or charge supply will be depleted very shortly. Therefore, the time to EOS is reported to the implantable medical device 200 and/or to the external device 270 (block 740). The ERI is also reported to the implantable medical device 200 and/or to the external device 270, which is then brought to the attention of the patient and/or a medical professional.

In addition to battery life, for diagnostic purposes the impedance of the various leads that deliver stimulation provided by the IMD 200 is also of interest. Lead impedance measurements and known output current signal characteristics may be used to calculate consumed stimulation charge. Sudden changes in lead impedance may indicate any of a number of changes in the operation of the implantable medical device 200. Changes in impedance may indicate that the leads delivering the stimulation have moved or have been damaged, or that the patient's body where the stimulation was delivered may have changed in some way.

Figure 1C:
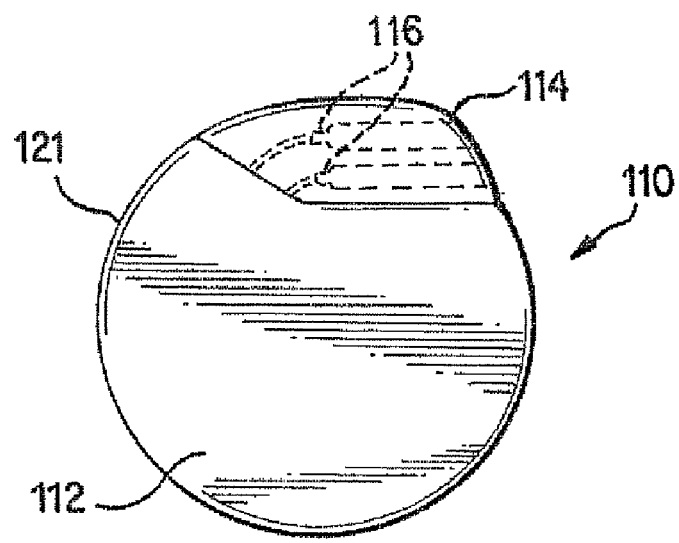
FIG. 1C illustrates an implantable medical device suitable for use in the present invention, showing the header and electrical connectors for coupling the device to a lead/electrode assembly.
Figure 1D:
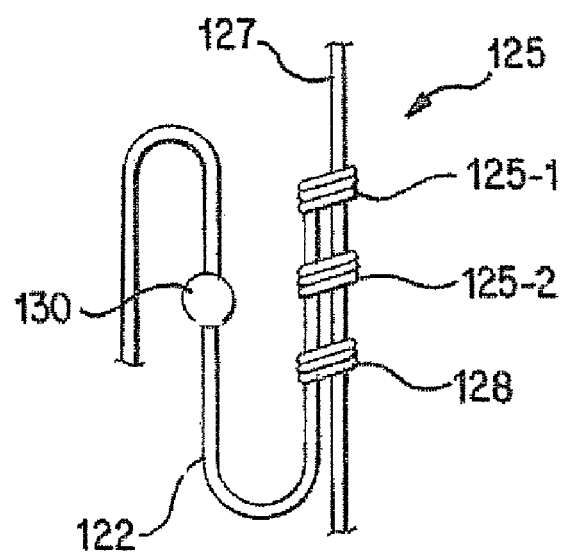
FIG. 1D shows a lead and electrodes suitable for use in the present invention attached to a vagus nerve of a patient.
Figure 8:
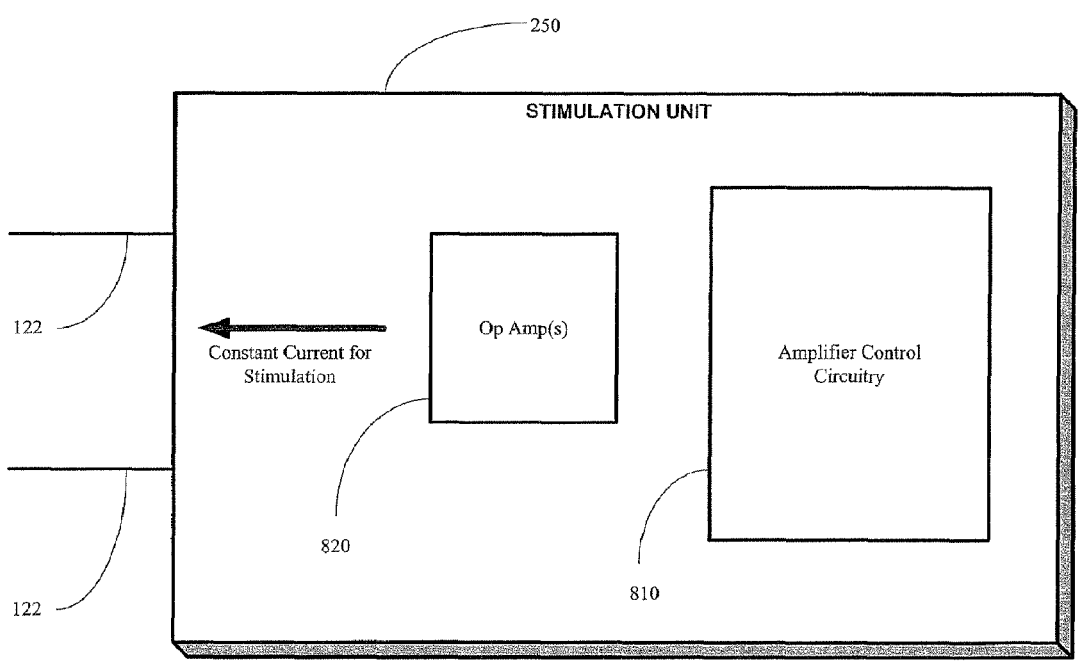
FIG. 8, is a block diagram of the stimulation unit shown in FIG. 2, in accordance with one illustrative embodiment of the present invention.

Turning now to FIG. 8, a block diagram is provided depicting in further detail an embodiment of the stimulation unit 250 of FIG. 2. The stimulation unit 250 of the IMD 200 comprises an op amp unit 820, which may comprise one or more operational amplifiers that are capable of delivering a controlled current signal for stimulation. In one embodiment, the controlled current is a constant current or a substantially constant current. The stimulation unit 250 may also comprise an amplifier control circuitry unit 810 that may contain circuitry and/or programmable logic to control the operation of the op amps 820. Additionally, the stimulation unit 250 may be coupled to leads 122, which may comprise a pair of signal wires capable of delivering an electrical signal to an electrode pair 125-1 and 125-2 (FIG. 1D) each coupled to a distal end of one of the leads 122. The leads 122 (and the electrodes 125-1 and 125-2) are capable of providing a complete circuit between the implantable medical device 200 and the region of the body/tissue to which the electrodes are attached, which may be approximated as an equivalent impedance. Each lead 122 may comprise a single strand wire or, more preferably, a multi-strand wire braided or otherwise coupled together as a single functional wire. Each of the two lead wires 122 in this embodiment is provided with a separate socket and connector 116, as shown in FIG. 1C. In another embodiment, two leads 122 may be combined into a single coaxial cable (as shown in FIGS. 1A and 1D), with a single socket providing both coaxial connectors 116.

Embodiments of the present invention provide for utilizing the delivery of a constant current signal for delivery of stimulation, and measurement of the impedance experienced by the leads 122. In a preferred embodiment, the controlled or constant current signal provided by the stimulation unit 250 is independent of the impedance experienced across the leads 122. For example, even if the impedance experienced across the leads 122 changes, the op amp 820, in conjunction with the amplifier control circuitry 810, adjusts to deliver a controlled or constant current despite the change in the impedance experienced across the leads 122.

Since a controlled, constant current is delivered despite variations in the impedance across the leads 122, the voltage across the lead terminals provide an indication of the lead impedance. For example, if the nerve tissue to which the leads 122 are connected has an impedance of 1000 ohms, a particular stimulation may call for a one milliamp constant current signal. In this case, even if a 5000 ohms impedance is experienced across the leads 122, the stimulation unit 250 will still provide a one milliamp current. Hence, the power may vary but the current remains constant. In other words, the op amp 820 will stabilize itself utilizing various circuitry, including the amplifier control circuitry 810, to provide a constant current signal even if the impedance experienced by the leads 122 varies during the period the signal is provided. Therefore, using Ohm's Law, V=IR, a measurement of the voltage across the leads 122 will provide an indication of the actual impedance experienced by the leads 122.

Figure 9:
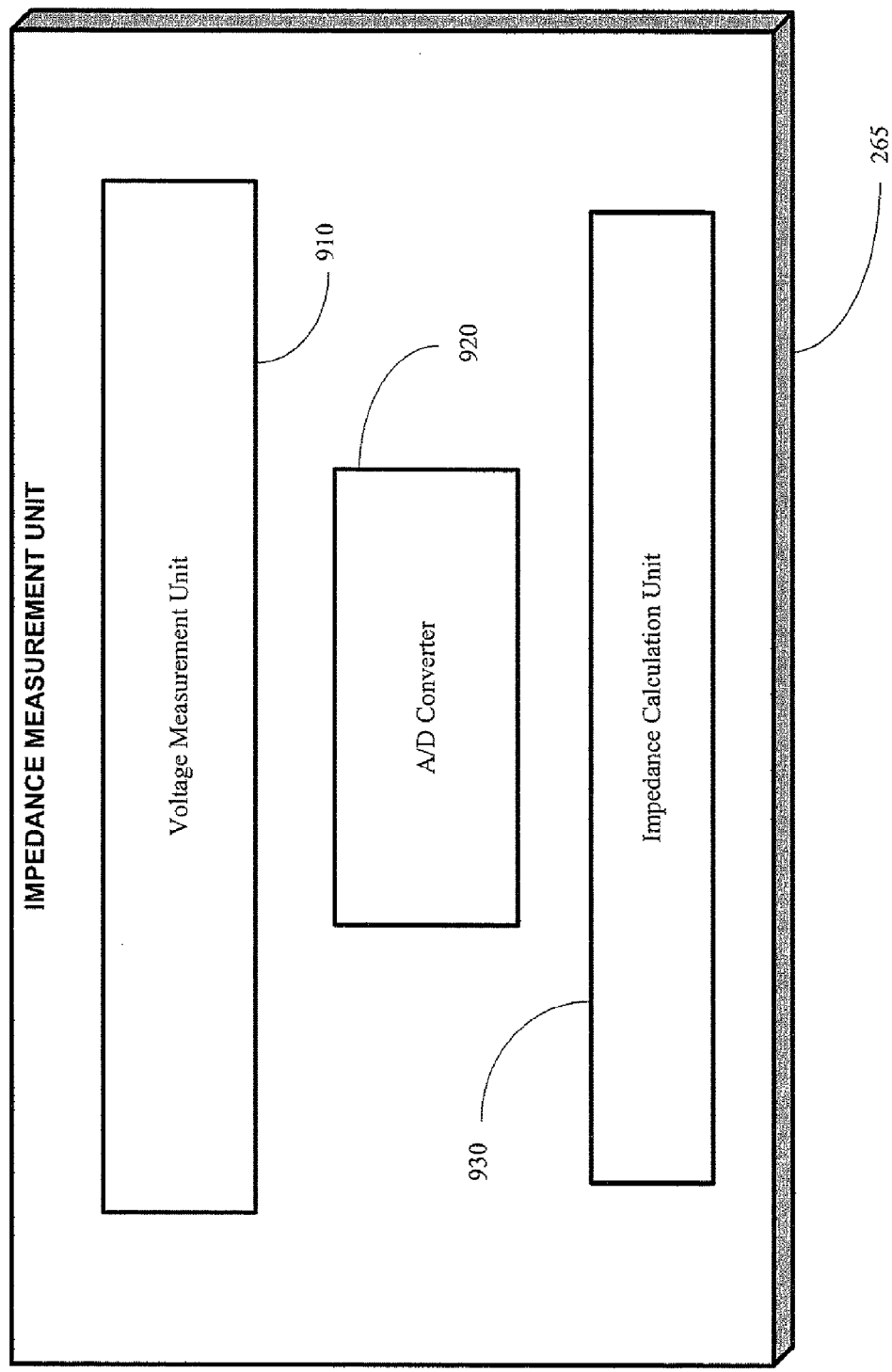
FIG. 9 is a block diagram of the impedance measurement unit shown in FIG. 2, in accordance with one illustrative embodiment of the present invention.

Turning now to FIG. 9, a block diagram depiction of one embodiment of the impedance measurement unit 265 from FIG. 2 is provided. In one embodiment, the impedance measurement unit 265 comprises a voltage measurement unit 910, an A/D converter (analog to digital converter) 920 and an impedance calculation unit 930. The voltage measurement unit 910 is capable of measuring or determining the voltage differential between the terminals of the leads 122. The signal from the voltage measurement unit 910 is generally an analog signal, which may be sent to the A/D converter 920. The A/D converter 920, which preferably has been calibrated prior to the operation of the IMD 200, will convert the analog voltage measurement signal to a digital signal. In alternative embodiments of the present invention the impedance measurement unit 265 may be implemented without the use of the A/D converter 920 and still remain within the scope of the present invention.

Although certain embodiments may be implemented without it, the A/D converter 920 may be beneficial for enhancing the resolution of the voltage signal, thereby providing for enhanced analysis of the voltage across the leads 122. Based upon the voltage across the leads 122, and the constant current signal provided by the stimulation unit 250, the impedance calculation unit 930 calculates the impedance by dividing the voltage across the lead terminals 122 by the current delivered by the stimulation unit 250. The impedance calculation unit 930 may be a hardware unit, a software unit, a firmware unit, or any combination thereof, which may be located in various portions of the IMD 200, including in the impedance measurement unit 265, in the stimulation controller 230, in the power source controller 220, or in any other portion of the IMD 200.

In an alternative embodiment, the calculation described as being performed by the impedance calculation unit 930 may alternatively be performed by the external unit 270, which may receive the signal relating to the constant current stimulation signal and the measured voltage signal. One of the advantages of utilizing the embodiments provided by the present invention is that substantially any size of a constant or controlled current stimulus signal may be used to perform the impedance measurement, thereby conserving battery power of the implantable medical device 200. Accordingly, the smallest stimulation signal that may reliably be provided by the stimulation unit 250 may be used to perform the impedance measurement. Thus, the impedance measurement may be made without imposing a significant charge depletion burden on the battery. Additionally, the impedance of the leads 122 themselves is also accounted for when analyzing the impedance. Furthermore, the A/D converter 920 may be calibrated prior to the operation of the implantable medical device 200, for example, during the manufacturing process.

Turning again to FIGS. 1A-1D, the leads 122 are shown connected to tissue (e.g., nerve tissue 127) in a patient's body and to the IMD 200. The implantable medical device 200 may comprise a main body 112 (FIG. 1A) in which the electronics described in FIG. 2 are enclosed. Coupled to the main body 112 is a header 114 (FIG. 1A) designed with terminal connectors 116 (FIG. 1C) for connecting to leads 122. The main body 112 may comprise a titanium case 121 and the header 114 may comprise a biocompatible polymer such as polyurethane or acrylic. The leads 122 projecting from the header 114 may be attached to the tissue utilizing a variety of methods for attaching the leads 122 to tissue. A first end of the leads 122 is coupled to connector(s) 116 on the header 114, and a distal end is coupled to the tissue by electrodes 125-1 and 125-2, which together provide a cathode and an anode (FIG. 1D). Therefore, the current flow may take place from one electrode 125-1 to a second electrode 125-2 via the tissue, thereby delivering the stimulation.

The system illustrated in FIGS. 1A-1D may be viewed as an electrical circuit that includes a current or voltage source (i.e., the battery 210 of the IMD 200) being connected to an impedance (i.e., the equivalent impedance of the tissue) via a pair of wires (i.e., the leads 122). The total impedance connected to the IMD 200 includes the impedance of the lead wires 122 as well as the impedance across the terminals 116 of the leads 122 to the tissue. One of the biggest components of the impedance experienced by terminals 116 on the header 114, to which the leads 122 are connected, is the impedance of the tissue. Therefore, if a break in any one portion of the lead wires 122 occurs (such as a break in one or more strands of a multistrand wire), the impedance may rise significantly, which may provide an indication that a break in the lead wire 122 has occurred.

Figure 10:
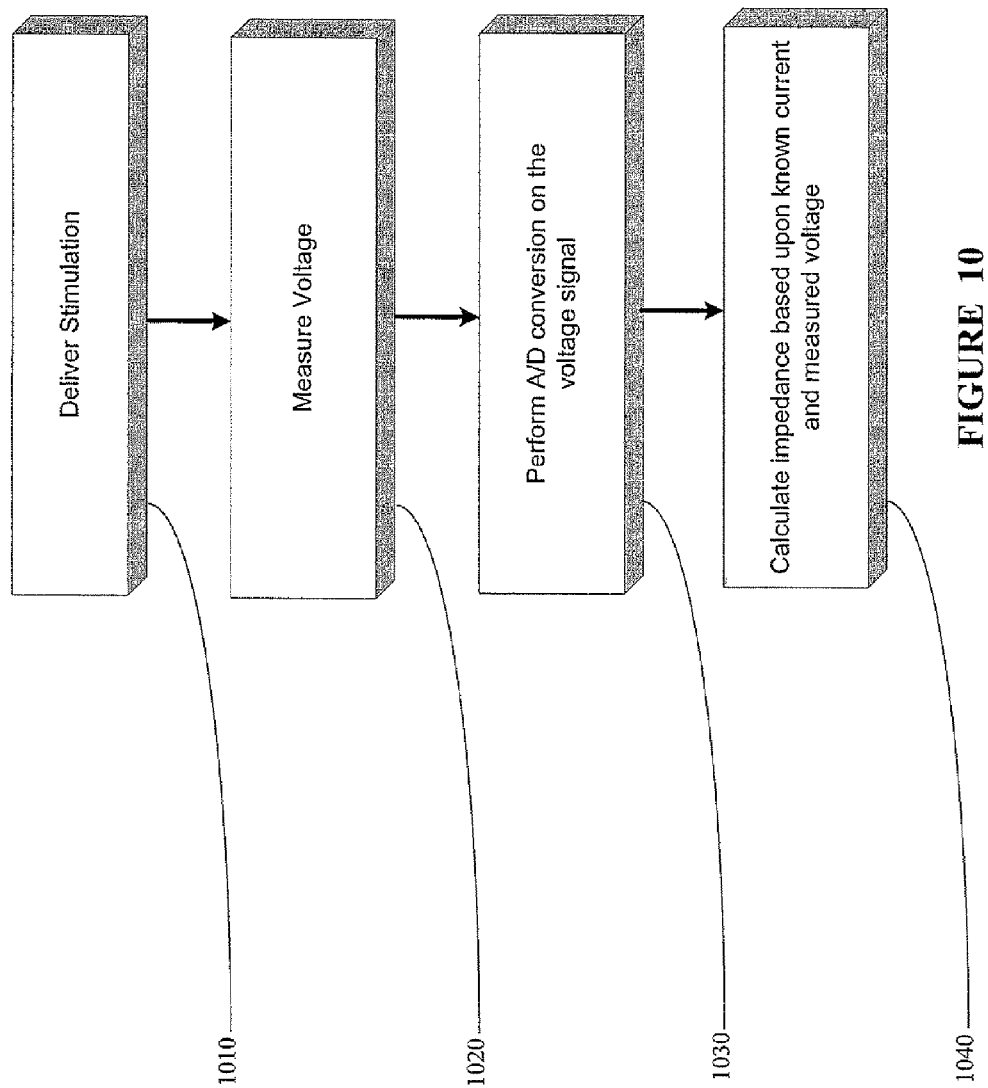
FIG. 10 is a flowchart of a method of performing an impedance measurement, in accordance with one illustrative embodiment of the present invention.

Turning now to FIG. 10, a flowchart depicting steps for determining the impedance experienced by the leads 122 of the IMD 200 is provided. As shown in step 1010, stimulation is delivered by the IMD 200 to the tissue of the patient by one of a number of available stimulation delivery modes, such as a constant current signal pulse (step 1010). To conserve battery power, impedance may be determined using a small magnitude and/or short duration pulse. The resultant voltage induced across the leads 122 is measured (block 1020) upon delivery of the stimulation signal. Voltage measurement may be performed by a voltage measurement unit 910 (FIG. 9) during delivery of the stimulation current signal. The IMD 200 adjusts the time at which the voltage is measured such that it occurs while the stimulation current signal is being delivered.

An analog-to-digital (A/D) conversion is preferably performed on the voltage signal (block 1030). Although, embodiments of the present invention may be performed without utilizing an A/D converter 920, in a preferred embodiment an A/D converter 920 (FIG. 9) is used to provide precise resolution of the voltage signal. The A/D converter 920 is preferably calibrated prior to the conversion of the voltage signal from analog to digital. Finally, the impedance is calculated utilizing the amplitude of the current delivered for stimulation and the corresponding voltage measurement, as shown in step 1040. The voltage resulting from the current signal delivered as stimulation is divided by the value of the current to arrive at the total impedance across the terminals 116 of the header 114 (FIGS. 1A-1D). In one embodiment, the predetermined impedance of the lead 122 itself may be subtracted to arrive at the impedance across the lead terminals 116, which corresponds to the impedance of the tissue 1030. Various operational adjustments to the operation of the IMD 200 may be made based upon the determination of the impedance across the terminals 116.

Figure 11:
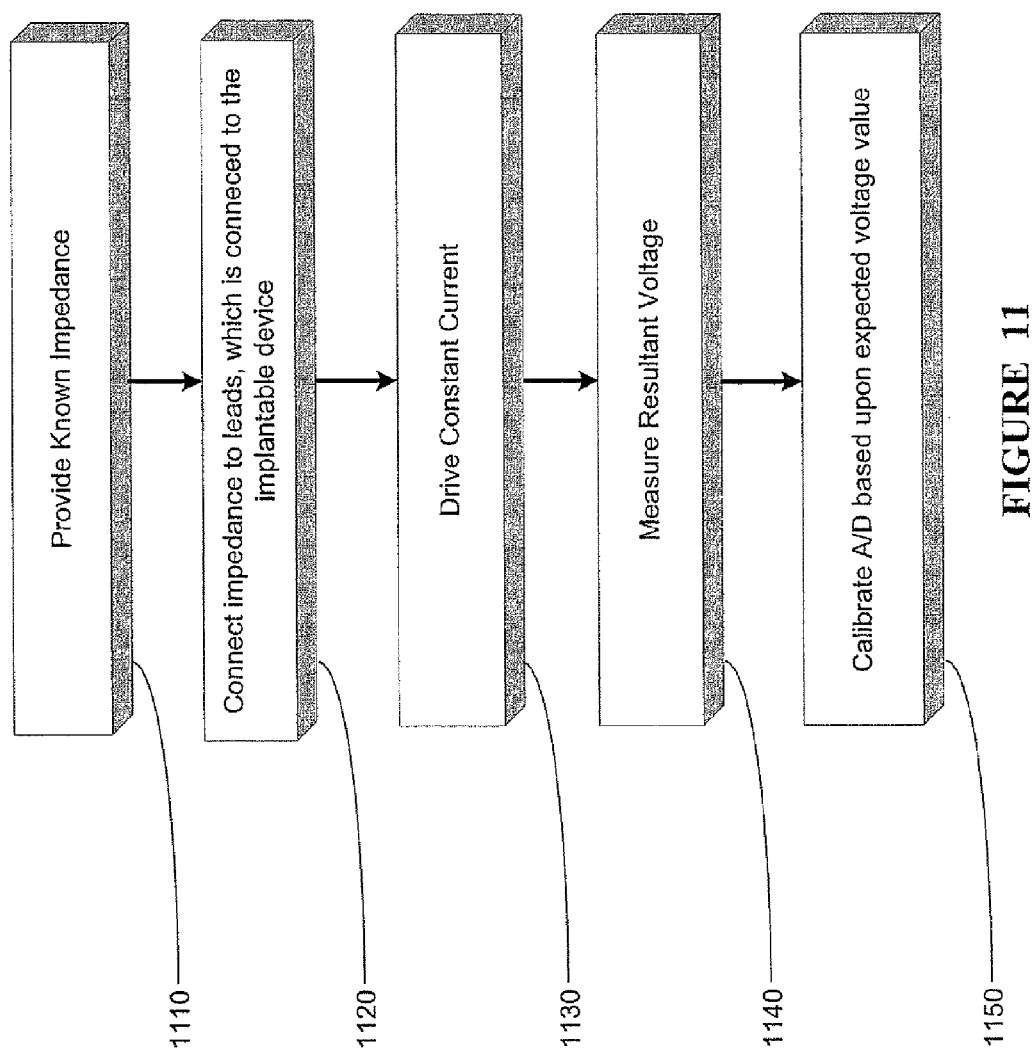
FIG. 11 is a flowchart of a method of performing a calibration of an A/D converter used for impedance measurement, in accordance with one illustrative embodiment of the present invention.

FIG. 11 provides a flowchart depicting the steps for performing the calibration of the A/D converter 920 (FIG. 9). In a preferred embodiment, the calibration of the A/D converter 920 is performed prior to implanting the IMD 200 in the body of the patient, more preferably during the manufacturing process of the IMD 200. Referring to FIG. 11, a predetermined, known impedance is provided for the calibration of the A/D converter 920, as depicted in step 1110. The known impedance is electrically connected across the two distal ends of leads 122 (which may or may not include electrode assembly 125), and the other ends of the lead wires 122 are connected to the terminals 116 of header 114 (step 1220). With the leads 122 connected between the IMD 200 and the known impedance, a constant current test signal is driven through the lead 122, through the known impedance, and back to the IMD 200 (step 1130).

The constant current test signal may comprise a series of individual constant current signals that may vary in duration of current amplitude from one signal to another in the series of test signals, provided that each individual test pulse comprises a constant current. During the delivery of each constant current test pulse to the known impedance, a corresponding voltage resulting from the driving of the constant current is measured across the terminals 116 of the IMD 200 (step 1240). This measurement of voltage at the terminals 116 allows a comparison to a theoretical indication of what the measurement should be by calculation from the known current being driven, and the known impedance across the leads 122. This theoretical voltage calculation value is then used with the actual voltage measured across the terminals 116 to calibrate the A/D converter 920 (block 1150). Calibration of the A/D converter 920 should provide improved accuracy for measurements subsequently processed by the A/D converter 920. In another embodiment, the calibration process may be performed using multiple known impedances and corresponding resulting multiple measured voltages. Such a calibration over a range of impedances may provide further improved accuracy.

Utilizing embodiments of the present invention, a more accurate assessment of the status of the battery and the impedance experienced by the leads 122 may be assessed, thereby providing better warnings to the user and/or to a healthcare provider assessing the operations of the IMD 200. Various end of service signals (EOS) and/or elective replacement indication (ERI) signals may be provided to indicate the status of the operation of the IMD 200. Additionally, the impedance experienced by the leads 122 of the IMD 200 may be analyzed to assess the integrity of the leads 122 or any drastic changes in the tissue to which the stimulation signal is provided.

The particular embodiments disclosed above are illustrative only, as the invention may be modified and practiced in different but equivalent manners apparent to those skilled in the art having the benefit of the teachings herein. Furthermore, no limitations are intended to the details of construction or design herein shown, other than as described in the claims below. The particular embodiments disclosed above may be altered or modified and all such variations are considered within the scope and spirit of the invention. Accordingly, the protection sought herein is as set forth in the claims below.

What is claimed:

1. A method for determining the remaining useful life of an energy storage device in an implantable medical device, said energy storage device having a total available electrical charge that may be obtained from said energy storage device, said method comprising:
   determining an active charge depletion of the implantable medical device;
   determining an inactive charge depletion of said implantable medical device; and
   determining a time period until an end of service of the energy storage device based upon said active charge depletion, said inactive charge depletion, and said total available charge, wherein determining an active charge depletion of an implantable medical device further comprises determining a charge depleted during a previous stimulation performed by said implantable device and determining an active current usage rate for a future stimulation to be performed by said implantable device, wherein determining an active current usage rate for a future stimulation to be performed by said implantable medical device further comprises correlating a first predetermined current usage rate with a first stimulation performed by said implantable device.

2. The method of claim 1, wherein correlating said first predetermined current usage rate with said first stimulation performed by said implantable device further comprises calibrating said first predetermined current usage rate based upon at least one stimulation parameter.

3. The method of claim 1, wherein correlating said first predetermined current usage rate with said first stimulation performed by said implantable device further comprises calibrating said first predetermined current usage rate based upon a lead impedance.

4. The method of claim 1, wherein determining an active current usage rate for a future stimulation to be performed by said implantable medical device further comprises correlating a second predetermined current usage rate with a second stimulation performed by said implantable device.

5. The method of claim 4, wherein correlating said second predetermined current usage rate with said second stimulation performed by said implantable device further comprises calibrating said second predetermined current usage rate based upon at least one stimulation parameter.

6. A method for determining the remaining useful life of an energy storage device in an implantable medical device, said energy storage device having a total available electrical charge that may be obtained from said energy storage device, said method comprising:
   determining an active charge depletion of the implantable medical device;
   determining an inactive charge depletion of said implantable medical device; and
   determining a time period until an end of service of the energy storage device based upon said active charge depletion, said inactive charge depletion, and said total available charge, wherein determining an inactive charge depletion of an implantable medical device further comprises determining a charge depleted during a previous idle period of said implantable medical device.

7. A method for determining the remaining useful life of an energy storage device in an implantable medical device, said energy storage device having a total available electrical charge that may be obtained from said energy storage device, said method comprising:
   determining an active charge depletion of the implantable medical device;
   determining an inactive charge depletion of said implantable medical device; and
   determining a time period until an end of service of the energy storage device based upon said active charge depletion, said inactive charge depletion, and said total available charge, wherein determining an inactive charge depletion of said implantable medical device further comprises determining an idle current usage rate for a future idle period of said implantable medical device.

8. The method of claim 7, further comprising calibrating said idle current usage rate for a previous idle time period.

9. The method of claim 1, wherein said energy storage device comprises a battery.

10. The method of claim 1, further comprising generating an end of service signal based upon a determination that said time period until said end of service equals zero.

11. The method of claim 1, further comprising generating an end of service signal based upon a determination that said end of service has already occurred.

12. The method of claim 11, further comprising generating an elective replacement indicator signal based upon a determination that said time period until said end of service is less than or equal to a predetermined period.

13. The method of claim 12, wherein said predetermined period is six months.

14. The method of claim 6, wherein said energy storage device comprises a battery.

15. The method of claim 6, further comprising generating an end of service signal based upon a determination that said time period until said end of service equals zero.

16. The method of claim 6, further comprising generating an end of service signal based upon a determination that said end of service has already occurred.

17. The method of claim 16, further comprising generating an elective replacement indicator signal based upon a determination that said time period until said end of service is less than or equal to a predetermined period.

18. The method of claim 17, wherein said predetermined period is six months.

19. The method of claim 7, wherein said energy storage device comprises a battery.

20. The method of claim 7, further comprising generating an end of service signal based upon a determination that said time period until said end of service equals zero.

21. The method of claim 7, further comprising generating an end of service signal based upon a determination that said end of service has already occurred.

22. The method of claim 21, further comprising generating an elective replacement indicator signal based upon a determination that said time period until said end of service is less than or equal to a predetermined period.

23. The method of claim 22, wherein said predetermined period is six months.

\* \* \* \* \*